US008394986B2

(12) United States Patent
Bonnert et al.

(10) Patent No.: US 8,394,986 B2
(45) Date of Patent: Mar. 12, 2013

(54) PHENOXIACETIC ACID DERIVATIVES

(75) Inventors: Roger Victor Bonnert, Loughborough (GB); Anil Patel, Loughborough (GB); Stephen Thom, Loughborough (GB)

(73) Assignee: AstraZeneca AB, Cheshire (GB)

( * ) Notice: Subject to any disclaimer, the term of this patent is extended or adjusted under 35 U.S.C. 154(b) by 0 days.

(21) Appl. No.: 13/190,881

(22) Filed: Jul. 26, 2011

(65) Prior Publication Data

US 2011/0281898 A1 Nov. 17, 2011

Related U.S. Application Data

(63) Continuation of application No. 10/569,065, filed as application No. PCT/GB2004/003551 on Aug. 18, 2004, now Pat. No. 8,003,703.

(30) Foreign Application Priority Data

Aug. 21, 2003 (SE) .................................... 0302281
Jun. 4, 2004 (GB) .................................. 0412448.3

(51) Int. Cl.
C07C 63/04 (2006.01)
(52) U.S. Cl. ..................................................... 562/493
(58) Field of Classification Search ................... 562/493
See application file for complete search history.

(56) References Cited

U.S. PATENT DOCUMENTS

| | | | |
|---|---|---|---|
| 3,278,524 A | 10/1966 | Johnson et al. |
| 3,920,846 A | 11/1975 | Hanauye et al. |
| 3,954,852 A | 5/1976 | Shen et al. |
| 3,985,779 A | 10/1976 | Tanaka et al. |
| 4,234,742 A | 11/1980 | Cognacq et al. |
| 4,248,618 A | 2/1981 | Serban et al. |
| 4,670,566 A | 6/1987 | Walsh |
| 5,006,542 A | 4/1991 | Hall et al. |
| 5,145,790 A | 9/1992 | Mattingly et al. |
| 5,411,972 A | 5/1995 | Komoto et al. |
| 5,413,891 A | 5/1995 | Matsuura et al. |
| 5,532,371 A | 7/1996 | Komoto et al. |
| 5,703,099 A | 12/1997 | Hamanaka et al. |
| 6,057,408 A | 5/2000 | Winter et al. |
| 6,150,413 A | 11/2000 | Bernardon et al. |
| 6,376,546 B1 | 4/2002 | Shoda et al. |
| 6,417,212 B1 | 7/2002 | Brooks et al. |
| 7,056,942 B2 | 6/2006 | Hildesheim et al. |
| 7,067,507 B2 | 6/2006 | Pullet et al. |
| 7,737,135 B2 | 6/2010 | Luker et al. |
| 8,003,703 B2 | 8/2011 | Bonnert et al. |
| 8,008,350 B2 | 8/2011 | Luker et al. |
| 8,022,248 B2 | 9/2011 | Bonnert et al. |
| 2003/0050320 A1 | 3/2003 | Hashimoto et al. |
| 2004/0029933 A1 | 2/2004 | Zhao et al. |
| 2004/0097555 A1 | 5/2004 | Ohkawa et al. |
| 2004/0220237 A1 | 11/2004 | Fu et al. |
| 2005/0239881 A1 | 10/2005 | Dunn et al. |
| 2006/0211765 A1 | 9/2006 | Pairaudeau et al. |
| 2006/0264435 A1 | 11/2006 | Bonnert et al. |
| 2006/0293352 A1 | 12/2006 | Bonnert et al. |
| 2007/0249686 A1 | 10/2007 | Bonnert et al. |
| 2008/0114002 A1 | 5/2008 | Bonnert et al. |
| 2008/0132480 A1 | 6/2008 | Luker et al. |
| 2008/0255150 A1 | 10/2008 | Luker |
| 2008/0293775 A1 | 11/2008 | Bonnert et al. |
| 2009/0012151 A1 | 1/2009 | Bonnert et al. |
| 2009/0036535 A1 | 2/2009 | Luker et al. |
| 2009/0149448 A1 | 6/2009 | Alcaraz et al. |
| 2009/0192163 A1 | 7/2009 | Luker et al. |
| 2010/0160285 A1 | 6/2010 | Luker et al. |
| 2011/0152374 A1 | 6/2011 | Luker et al. |

FOREIGN PATENT DOCUMENTS

| | | |
|---|---|---|
| CH | 432119 | 9/1967 |
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |

(Continued)

OTHER PUBLICATIONS

Vippagunta, et al. Advanced Drug Delivery Reviews 48 (2001) 3-26.* Amin et al., "The Fries Reaction: Part VI—the rearrangement of aryl p-toluene-sulphonates & a convenient method for synthesis of hydroxyl-diarylsulphones", *Journal of Scientific Industrial Research*, vol. 13B, 1954, pp. 181-183.

Atkinson et al., "Substituted (2-Phenoxyphenyl)acetic Acids with Antiinflammatory Activity", *J. Med. Chem.*, vol. 26, 1983, pp. 1353-1360.

AstraZeneca AB: WO03066046 & WO03066047, "The use of indole-3-acetic acids as CRTH2 receptor antagonists", *Expert Opin. Ther. Patents* 14(1):125-128 (2004).

Baliah et al., "Fries rearrangement of the benzenesulphonates of xylenols", *Recueil des Travaux Chimiques des Pays-Bas*, vol. 80, 1961, pp. 139-148.

(Continued)

*Primary Examiner* — Shawquia Young

(74) *Attorney, Agent, or Firm* — Fish & Richardson P.C.

(57) ABSTRACT

The invention relates to substituted phenoxyacetic acids as useful pharmaceutical compounds for treating respiratory disorders, pharmaceutical compositions containing them, and processes for their preparation.

4 Claims, No Drawings

FOREIGN PATENT DOCUMENTS

| | | |
|---|---|---|
| WO | WO 01/81312 | 11/2001 |
| WO | WO 01/92224 | 12/2001 |
| WO | WO 02/094770 | 11/2002 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.

Berhenke et al., "Some Aryloxyaliphatic Acids", *Journal of the American Chemical Society* 73:4458 (1951).

Brown et al., "Some Chlorinated Hydroxyphenoxyacetic Acids", *Journal of the Chemical Society*, 1955, pp. 3681-3687.

Budavari, S., "The merck Index, 13$^{th}$ edition", p. 3106, monograph 3108, XP-002347170, 2001.

Burger, "Isosterism and bioisosterism in drug design", in Progress in Drug Research 287-328 (Ernst Jucker, ed., Birkhauser Verlag, 1991).

Cavill et al., "The chemistry of plant-growth regulators. Part I. 2:4-dichloro-6-hydroxyphenoxyacetic acid and related compounds", *Journal of the Chemical Society*, 1954, pp. 565-569.

*Cecil Textbook of Medicine*, 20$^{th}$ ed. (1996), vol. 2, pp. 1992-1996.

*Cecil Textbook of Medicine*, 20$^{th}$ ed. (1996), vol. 2, pp. 2050-2057.

Chemical abstract 123:213132 in CAS (or JP07140725), 1995.

Chemical abstract 123:22081 in CAS (or EP622690), 1994.

Chemical abstract 116:123167 in CAS (or EP455058), 1993.

Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).

Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).

Chemical abstract 49:86470 in CAS or Mel'nikov et al., "Structure and physiological activity of alkyl- and aryl-phenoxyacetic acids and their derivatives", Fiziologiya Rastenii 2:267-70 (1955).

Chemical abstract 35:37645 in CAS or Hazlet et al., "The Bromination of 2-Phenylphenyl Acetate", Journal of the American Chemical Society 63:1890-2 (1941).

Chiu et al., "Derivation and Properties of Recombinant Fab Antibodies to Coplanar Polychlorinated Biphenyls", *J. Agric. Food Chem.* 48:2614-2624 (2000).

Clemo et al., "Strychnine and brucine. Part II", *Journal of the Chemical Society*, vol. 125, 1924, pp. 1751-1804, XP008053173.

Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.

Coxworth, "Synthesis of Chlorinated 2-(3-Benzofuranyl)Phenols", *Canadian Journal of Chemistry* 44:1092-1096 (1966).

Dalal et al., "Synthetic insecticides. I. Synthesis of α, α-bis(aryl)-β, β, γ-trichlorobutanes", STN Accession No. 1950:35789, Document No. 44:35789, Abstract of Journal of the Indian Chemical Society 26:549-52 (1949).

"DialogWeb Records", http://www.dialogweb.com/cgi/document?req=1284661379410, accessed Sep. 16, 2010.

Ebenezar et al., "Prostaglandins in the patent literature", *Expert Opin. Ther. Patents* 17(9):1131-1145 (2007).

FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.

Fromageot et al., "Photodecarboxylation of 2-(2'-carboxymethoxy-5'-methylphenyl)-benzotriazole", *Journal of Photochemistry and Photobiology, A: Chemistry* 44(1):93-98 (1988).

Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.

Gaunt et al., "Metabolism of 4-chloro-2-methylphenoxyacetate by a soil pseudomonad", *Biochem. J.*, vol. 122, 1971, pp. 519-526.

Gavezzotti, "Are Crystal Structures Predictable?", *Acc. Chem. Res.* 27:309-314 (1994).

Golub et al., "Molecular Classification of Cancer: Class Discovery and Class Prediction by Gene Expression Monitoring", *Science* 286:531-537 (1999).

Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", *J. Med. Chem.*, vol. 44, 2001, pp. 1758-1776.

Hazlet et al., "Bromination of 2-phenylphenyl acetate", STN Accession No. 1941:37645, Document No. 35:37645, Abstract of Journal of the American Chemical Society 63:1890-2 (1941).

Hazlet et al., "The Bromination of 2-Phenylphenyl Acetate", *Journal of the American Chemical Society* 63:1890-1892 (1941).

Huston et al., "Chloro derivatives of o- and p-benzyl phenols. II. Some monochloro, dichloro and trichloro derivatives of ortho and para benzyl phenols", *Journal of the American Chemical Society*, vol. 55, No. 11, 1933, pp. 4639-4643.

Inukai et al., "*ortho*-Disubstituted *F*-benzenes. III. Preparation of (*F*-benzo)heterocyclic compounds from *F*-benzoic acid and *F*-phenol, and the reactions of some intermediary *F*-benzoyl- and F-phenoxy compounds", *Bull. Chem. Soc. Jpn.*, vol. 54, No. 11, 1981, pp. 3447-3452.

Janczewski et al., "Effect of Molecular Structure on Optical Properties of Sulfoxide Systems. O-Phenoxyphenylsulfinylacetic Acid and some of Their Derivatives. Part II", *Polish Journal of Chemistry*, vol. 62, No. 1-3, 1964, pp. 91-105, XP008053171.

Kmonicek et al., "(Tert-Amino)-11-(4-Methylpiperazino)Dibenzo[b,f]Thiepins and their 10,11-Dihydro Derivatives; Synthesis and Neuroleptic Activity", *Collection Czechoslov. Chem. Commun.*, vol. 52, 1987, pp. 792-803, XP-002347166.

Lehmler et al., "Synthesis of hydroxylated PCB metabolites with the Suzuki-coupling", *Chemosphere*, vol. 45, 2001, pp. 1119-1127.

Litvak et al., "Synthesis and S$_N$Ar reactions of new dioxins and predioxins", *Chemosphere*, vol. 43, No. 4-7, 2001, pp. 493-495.

Lupus erythematosus [online], [retrieved Dec. 28, 2006]. Retrieved from the Internet, URL; http://en.wikipedia.org/wiki/Lupus_erythematosus>.

Ly et al., "Small-molecule CRTH2 antagonists for the treatment of allergic inflammation: an overview", *Expert Opin. Invest. Drugs* 14(7):769-773 (2005).

Maeda et al., "Studies on the Synthesis and Analgesic and Anti-inflammatory Activities of 2-Thiazolylamino- and 2-Thiazolyloxy-arylacetic Acid Derivatives", *Chem. Pharm. Bull.*, vol. 31, No. 10, 1983, pp. 3424-3445, XP-002347167.

Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).

Manske et al., "Synthesis and Reactions of Some Dibenzoxepins", *Journal of American Chemical Society* 72:4797-4799 (1950).
Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.
Morissette et al., "High-throughput crystallization: polymorphs, salts, co-crystals and solvates of pharmaceutical solids", *Advanced Drug Delivery Reviews* 56:275-300 (2004).
Moser et al., "Synthesis and Quantitative Structure-Activity Relationships of Diclofenac Analogues", *J. Med. Chem.*, vol. 33, 1990, pp. 2358-2368, XP-001024801.
Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.
Ong et al., "Synthesis and Analgesic Activity of Some Spiro[dibenz[b,f]oxepin-10,4'-piperidine] Derivatives", *J. Med. Chem.*, vol. 22, No. 7,1979, pp. 834-839, XP-002347163.
Ono Pharm. Co. Ltd: WO03022813 & WO03022814, "The use of prostaglandin $D_2$ receptor antagonists to treat allergic rhinitis", *Expert Opin. Ther. Patents* 13(10):1657-1661 (2003).
Patani et al., "Bioisosterism: A Rational Approach in Drug Design", *Chem. Rev.* 96:3147-3176 (1996).
Rajsner et al., "Fluorinated tricyclic Neuroleptics: Synthesis and Pharmacology of 8-Fluoro-4-(4-Methylpiperazino)-4,5-Dihydrothieno[2,3-b]-1-Benzothiepin", *Collection Czechoslov. Chem. Commun.*, vol. 44, 1979, pp. 2997-3007, XP-002347164.
Ram et al., "Potential Hypolipidemic Agents Part VI: Synthesis and Biological Activity of Some New 4-Chloro/Methyl-2-pyrazolylphenoxy Alkanoates", *Indian Drugs* 29(6), 258-262 (1992).
Selvi et al., "Vilsmeier cyclization of 2-amino phenoxyacetic acid", *Synthetic Communications*, vol. 31, No. 14, 2001, pp. 2199-2202.
Sindelar et al., "Synthesis of 3-Chloro-5-(4-Methylpiperazino)-6,7-Dihydro-5H-Dibenzo[b,g]Thiocin, An Eight-Membered Ring Homologue of the Neuroleptic Agent Octoclothepin", *Collection Czechoslov. Chem. Commun.*, vol. 45, 1980, pp. 491-503, XP-002347160.
Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[b,f]Thiepin", *Collection Czechoslov. Chem. Commun.*, vol. 46, 1981, pp. 118-140, XP-002347168.
Sindler-Kulyk et al., "Synthesis of New 3-(Phenoxyphenyl)sydnones", *J. Hetercyclic Chem.*, vol. 29, No. 2, 1992, pp. 1013-1015, XP-002347161.
Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", *J. Med. Chem.* 29:852-855 (1986).
Thuillier, G., "Derives des acides 24 aryloxyacetiques a activite neurotrope", *Chimique Therapeutique*, vol. 1, No. 2, 1966, pp. 82-86.
Ueda et al., "The Synthesis of 10-(4-Methylpiperazino)dibenzo[b,f] thiepin and Related Compounds. Neurotropic and Psychotropic Agents", *Chem. Pharm. Bull.* 23(10):2223-2231 (1975).
Ulven et al., "Targeting of the Prostaglandin $D_2$ Receptors DP and CRTH2 for Treatment of Inflammation", *Current Topics in Medicinal Chemistry* 6:1427-1444 (2006).
Walsh et al., "Antiinflammatory Activity of N-(2-Benzoylphenyl)alanine Derivatives", *J. Med. Chem.*, vol. 27, 1984, pp. 1317-1321, XP-002347162.
Wheatley et al., "2-Benzylphenol Derivatives. III. Basic Ethers", *Journal of American Chemical Society*, vol. 71, No. 11, 1949, pp. 3795-3797.
Database CA [Online] Chemical Abstracts Service, Columbus, Ohio, US; XP002372494 retrieved from STN Database accession No. 1956:16264 abstract & Ott, Donald G. et al: "A carbon-14 tracer study of the alkaline rearrangement of chlorophenanthraquinones" Journal of the American Chemical Society, 77, 2325-9 CODEN:JACSAT; ISSN:0002-7863, 1955.
Database Caplus [Online] Chemical Abstracts Service, Columbus, Ohio, US; 1992, XP002372495 retrieved from STN Database accession No. 1992:255529 abstract & RAM, Bhagat et al: "Potential hypolipidemic agents part VI: synthesis and biological activity of some new 4-chloro/methyl-2-pyrazolylphenoxy alkanoates" Indian Drugs, vol. 29, No. 6, 1992, pp. 258-262.
Database WPI 1-3, 5, Section Ch, Week 200365 19, 20, Derwent Publications Ltd., London, GB, Class B03, AN 2003-689635 XP-002301315, WO03068744A1, Ishihara Sangyo Kaisha, Ltd., Aug. 21, 2003.
STN International, File Caplus, Caplus accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.
STN International, File Caplus, Caplus accession 1-5, 10, No. 1979:186607, document No. 90:186607, Ciba-Geigy, "Phenoxyphenoxyalkanecardoxylic acid derivatives", DE, A1, 2832435, 19790208.
STN International, File Caplus, Caplus accession 1-5, 10, No. 1971:53748, document No. 74:53748, Walker et al., "Synthesis of 5-phenyl-2,3,4,5-tetrahydro-1,4-benzoxazepines and corresponding 3-ones", & Journal of Organic Chemistry (1970), 36(2), 305-308.
STN International, File Caplus, Caplus accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.
STN International, File Caplus, Caplus accession 1-3, 5, 10, No. 1975:402045, document No. 83:2045, Shiley et al., "Fungicidal activity of some fluoroaromatic compounds", *Journal of Fluorine Chemistry* (1975), 5(4), 371-376.
STN International, File Caplus, Caplus accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.
STN International, File Caplus, Caplus accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.
STN International, File Caplus, Caplus accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.
STN Intenational, File Caplus, Caplus accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.
STN International, File Caplus, Caplus accession 1-7, 10, No. 1986:109631, document No. 104:109631, Yoshitomi Pharmaceutical Industries, Ltd., "Imidazole derivatives", JP, A2, 60142965, 19850729.
Vippagunta et al., "Crystalline solids", *Advanced Drug Delivery Reviews* 48:3-26 (2001).
Wermuth, "Molecular Variations Based on Isosteric Replacements", The Practice of Medicinal Chemistry, 1996, chapter 13, pp. 203-237.
Inflammatory Bowel Disease [online] [retrieved on Apr. 7, 2008 from the internet] URL:http://www.emedicinehealth.com/script/main/art.asp?articlekey=59121&pf=3&page=8.
Rheumatoid arthritis [online] [retrieved on Apr. 7, 2008 from the internet] URL:http://www.nlm.nih.gov/medlineplus/ency/article/000431.htm.
Asthma [online] [retrieved on May 30, 2008 from the Internet] URL:http://www.nlm.nih.gov/medlineplus/ency/article/000141.htm.
Rhinitis [online] [retrieved on Nov. 12, 2008 from the internet] URL:http://www.healthline.com/galecontent/rhinitis?print=true.
Preventing Asthma Symptoms [online] [retrieved on Apr. 23, 2010 from the internet] URL:http://www.webmd.com/asthma/guide/asthma-prevention.
Allergic Rhinitis—Prevention [online] [retrieved on Apr. 23, 2010 from the internet] URL:http://www.webmd.com/allergies/tc/allergic-rhinitis-prevention.

COPD Treatments: Improving Your Quality of Life [online] [retrieved on Apr. 23, 2010 from the internet] URL:http://www.webmd.com/lung/copd/copd-treatments-improving-your-quality-of-life.
RN 110624-55-0, retrieved from CAPLUS; retrieved on Apr. 7, 2008.
Database Beilstein chemical extract accession No. 6722243, Jan. 2010.
Database Beilstein chemical extract accession No. 6722682, Jan. 2010.
Database Beilstein chemical extract accession No. 3532059, Jan. 2010.
Database Beilstein chemical extract accession No. 2533336, Jan. 2010.
Database Beilstein chemical extract accession No. 2537173, Jan. 2010.
Database Beilstein chemical extract accession No. 3385275, Jan. 2010.
Database Beilstein chemical extract accession No. 3386554, Jan. 2010.
USPTO Office Action in U.S. Appl. No. 10/552,082, mailed Oct. 29, 2007, 6 pages.
Fish & Richardson P.C., Amendment in Reply to Action of Oct. 29, 2007 in U.S. Appl. No. 10/552,082, filed Feb. 29, 2008, 18 pages.
USPTO Final Office Action in U.S. Appl. No. 10/552,082, mailed Jun. 9, 2008, 18 pages.
Fish & Richardson P.C., Amendment in Reply to Action of Jun. 9, 2008 in U.S. Appl. No. 10/552,082, filed Sep. 9, 2008, 11 pages.
USPTO Office Action in U.S. Appl. No. 10/552,082, mailed Dec. 4, 2008, 23 pages.
Fish & Richardson P.C., Amendment in Reply to Action of Dec. 4, 2008 in U.S. Appl. No. 10/552,082, filed Apr. 6, 2009, 8 pages.
USPTO Notice of Allowance in U.S. Appl. No. 10/552,082, mailed Jul. 1, 2009, 9 pages.
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/552,082, mailed Jan. 7, 2010, 12 pages.
Fish & Richardson P.C., Amendment in Reply to Action of Jan. 7, 2010 in U.S. Appl. No. 10/552,082, filed Jul. 2, 2010, 8 pages.
USPTO Notice of Allowance in U.S. Appl. No. 10/552,082, mailed Sep. 15, 2010, 12 pages.
USPTO Office Action in U.S. Appl. No. 10/551,783, mailed Dec. 7, 2009, 15 pages.
Fish & Richardson P.C., Amendment in Reply to Action of Dec. 7, 2009 in U.S. Appl. No. 10/551,783, filed Mar. 8, 2010, 17 pages.
USPTO Office Action in U.S. Appl. No. 10/551,783, mailed Apr. 23, 2010, 9 pages.
Fish & Richardson P.C., Amendment in Reply to Action of Apr. 23, 2010 in U.S. Appl. No. 10/551,783, filed Jul. 2, 2010, 23 pages.
USPTO Notice of Allowance in U.S. Appl. No. 10/551,783, mailed Sep. 7, 2010, 6 pages.
Fish & Richardson P.C., RCE and IDS in reply to Notice of Allowance of Sep. 7, 2010 in U.S. Appl. No. 10/551,783, filed Dec. 6, 2010, 4 pages.
USPTO Office Action in U.S. Appl. No. 10/569,065, mailed May 4, 2007, 12 pages.
Fish & Richardson P.C., Amendment in Reply to Action of May 4, 2007 in U.S. Appl. No. 10/569,065, filed Aug. 3, 2007, 14 pages.
USPTO Final Office Action in U.S. Appl. No. 10/569,065, mailed Oct. 17, 2007, 4 pages.
Fish & Richardson P.C., Amendment in Reply to Action of Oct. 17, 2007 in U.S. Appl. No. 10/569,065, filed Jan. 17, 2008, 9 pages.
USPTO Office Action in U.S. Appl. No. 10/569,065, mailed Apr. 16, 2008, 14 pages.
Fish & Richardson P.C., Amendment in Reply to Action of Apr. 16, 2008 in U.S. Appl. No. 10/569,065, filed Jul. 16, 2008, 38 pages.
USPTO Office Action in U.S. Appl. No. 10/569,065, mailed Oct. 28, 2008, 15 pages.
Fish & Richardson P.C., Amendment in Reply to Action of Oct. 28, 2008 in U.S. Appl. No. 10/569,065, filed Jan. 27, 2009, 7 pages.
USPTO Office Action in U.S. Appl. No. 10/569,065, mailed May 13, 2009, 10 pages.
Fish & Richardson P.C., Amendment in Reply to Action of May 13, 2009 in U.S. Appl. No. 10/569,065, filed Jul. 14, 2009, 9 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Notice of Allowance in U.S. Appl. No. 10/569,065, mailed Sep. 1, 2010, 9 pages.
Fish & Richardson P.C., RCE and IDS in Reply to Notice of Allowance of Sep. 1, 2010 in U.S. Appl. No. 10/569,065, filed Nov. 8, 2010, 5 pages.
USPTO Notice of Allowance in U.S. Appl. No. 10/569,065, mailed Dec. 2, 2010, 10 pages.
Fish & Richardson P.C., RCE and IDS in Reply to Notice of Allowance of Dec. 2, 2010 in U.S. Appl. No. 10/569,065, filed Feb. 15, 2011, 5 pages.
USPTO Notice of Allowance in U.S. Appl. No. 10/569,065, mailed Apr. 8, 2011, 10 pages.
Fish & Richardson P.C., Response to Notice of Allowance of Apr. 8, 2011 in U.S. Appl. No. 10/569,065, filed Jul. 7, 2011, 2 pages.
USPTO Office Action in U.S. Appl. No. 11/571,707, mailed Mar. 12, 2010, 16 pages.
Fish & Richardson P.C., Amendment in Reply to Action of Mar. 12, 2010 in U.S. Appl. No. 11/571,707, filed Sep. 3, 2010, 14 pages.
USPTO Notice of Allowance in U.S. Appl. No. 11/571,707, mailed Nov. 22, 2010, 12 pages.
USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Final Office Action in U.S. Appl. No. 11/574,076, mailed Aug. 18, 2009, 7 pages.
Fish & Richardson P.C., RCE and Amendment in Reply to Action of Aug. 18, 2009 in U.S. Appl. No. 11/574,076, filed Dec. 18, 2009, 13 pages.
USPTO Notice of Allowance in U.S. Appl. No. 11/574,076, mailed Feb. 3, 2010, 12 pages.
Fish & Richardson P.C., Response to Notice of Allowance of Feb. 3, 2010 in U.S. Appl. No. 11/574,076, filed Apr. 30, 2010, 2 pages.
USPTO Office Action in U.S. Appl. No. 11/576,372, mailed Jul. 22, 2009, 19 pages.
Fish & Richardson P.C., Amendment in Reply to Action of Jul. 22, 2009 in U.S. Appl. No. 11/576,372, filed Jan. 22, 2010, 18 pages.
USPTO Final Office Action in U.S. Appl. No. 11/576,372, mailed May 7, 2010, 7 pages.
Fish & Richardson P.C., Reply to Action of May 7, 2010 in U.S. Appl. No. 11/576,372, filed Aug. 9, 2010, 10 pages.
USPTO Office Action in U.S. Appl. No. 11/576,372, mailed Sep. 2, 2010, 7 pages.
Fish & Richardson P.C., RCE, IDS and Amendment in Reply to Action of Sep. 2, 2010 in U.S. Appl. No. 11/576,372, filed Dec. 2, 2010, 16 pages.
USPTO Office Action in U.S. Appl. No. 11/719,832, mailed Apr. 30, 2010, 20 pages.
Fish & Richardson P.C., Amendment in Reply to Action of Apr. 30, 2010 in U.S. Appl. No. 11/719,832, filed Aug. 30, 2010, 18 pages.
USPTO Office Action in U.S. Appl. No. 11/719,832, mailed Oct. 6, 2010, 12 pages.
USPTO Office Action in U.S. Appl. No. 12/089,275, mailed Jan. 26, 2011, 25 pages.
USPTO Office Action in U.S. Appl. No. 12/089,276, mailed Jun. 17, 2009, 28 pages.

Fish & Richardson P.C., Amendment in Reply to Action of Jun. 17, 2009 in U.S. Appl. No. 12/089,276, filed Sep. 22, 2009, 10 pages.
USPTO Notice of Allowance in U.S. Appl. No. 12/089,276, mailed Jan. 4, 2010, 6 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Notice of Allowance in U.S. Appl. No. 12/089,276, mailed Sep. 21, 2010, 9 pages.
Fish & Richardson P.C., RCE and IDS in Reply to Notice of Allowance of Sep. 21, 2010 in U.S. Appl. No. 12/089,276, filed Dec. 20, 2010, 6 pages.
USPTO Notice of Allowance in U.S. Appl. No. 12/089,276, mailed Jan. 4, 2011, 11 pages.
USPTO Office Action in U.S. Appl. No. 12/092,431, mailed Aug. 4, 2009, 8 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
Fish & Richardson P.C., RCE, IDS and Amendment in Reply to Action of May 4, 2010 in U.S. Appl. No. 12/092,431, filed Sep. 7, 2010, 16 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
USPTO Final Office Action in U.S. Appl. No. 12/167,513, mailed Apr. 22, 2010, 22 pages.
Fish & Richardson P.C., Amendment in Reply to Action of Apr. 22, 2010 in U.S. Appl. No. 12/167,513, filed Oct. 22, 2010, 22 pages.
Petrillo et al., "$S_{RN}1$ C-Arylation of Potassium Aryloxides by Arylazo Phenyl or *Tert*-Butyl Sulfides in DMSO", Tetrahedron 46(23):7977-7990 (1990).
USPTO Office Action in U.S. Appl. No. 10/551,783, mailed May 17, 2011, 8 pages.
Fish & Richardson P.C., Terminal Disclaimers and Reply to Action of May 17, 2011 in U.S. Appl. No. 10/551,783, filed Nov. 16, 2011, 16 pages.
Fish & Richardson P.C., Response to Notice of Allowance of Nov. 22, 2010 in U.S. Appl. No. 11/571,707, filed Feb. 18, 2011, 12 pages.
USPTO Issue Notification in U.S. Appl. No. 11/571,707, mailed Mar. 30, 2011, 1 page.
Fish & Richardson P.C., RCE, Petition to Withdraw from Issue, and IDS in U.S. Appl. No. 11/571,707, filed Apr. 13, 2011, 7 pages.
USPTO Decision Granting Petition under 37 CFR 1.313(c)(2) in U.S. Appl. No. 11/571,707, mailed Apr. 14, 2011, 1 page.
USPTO Notice of Allowance in U.S. Appl. No. 11/571,707, mailed May 6, 2011, 11 pages.
Fish & Richardson P.C., Response to Notice of Allowance of May 6, 2011 in U.S. Appl. No. 11/571,707, filed Aug. 3, 2011, 3 pages.
USPTO Notice of Allowance in U.S. Appl. No. 12/642,244, mailed Sep. 6, 2011, 30 pages.
Fish & Richardson P.C., RCE and Amendment in Reply to Notice of Allowance of Sep. 6, 2011 in U.S. Appl. No. 12/642,244, filed Dec. 6, 2011, 9 pages.
USPTO Notice of Allowance in U.S. Appl. No. 12/642,244, mailed Jan. 31, 2012, 12 pages.
USPTO Non-Final Office Action in U.S. Appl. No. 11/576,372, mailed Dec. 5, 2011, 13 pages.
Fish & Richardson P.C., RCE, IDS and Amendment in Reply to Action of Oct. 6, 2010 in U.S. Appl. No. 11/719,832, filed Apr. 6, 2011, 27 pages.
Fish & Richardson P.C., Amendment in Reply to Action of Jan. 26, 2011 in U.S. Appl. No. 12/089,275, filed Jul. 26, 2011, 19 pages.
USPTO Notice of Allowance in U.S. Appl. No. 12/089,275, mailed Nov. 7, 2011, 18 pages.
Fish & Richardson P.C., RCE and IDS in Reply to Notice of Allowance of Jan. 4, 2011 in U.S. Appl. No. 12/089,276, filed Apr. 4, 2011, 4 pages.
USPTO Notice of Allowance in U.S. Appl. No. 12/089,276, mailed Apr. 12, 2011, 9 pages.
Fish & Richardson P.C., Response to Notice of Allowance of Apr. 12, 2011 in U.S. Appl. No. 12/089,276, filed Jul. 11, 2011, 2 pages.
USPTO Non-Final Office Action in U.S. Appl. No. 12/973,395, mailed Oct. 13, 2011, 19 pages.
USPTO Non-Final Office Action in U.S. Appl. No. 12/092,431, mailed Aug. 17, 2011, 13 pages.
USPTO Non-Final Office Action in U.S. Appl. No. 12/096,557, mailed Nov. 15, 2011, 30 pages.

* cited by examiner

PHENOXIACETIC ACID DERIVATIVES

CROSS-REFERENCE TO RELATED APPLICATIONS

This application is a continuation of U.S. patent application Ser. No. 10/569,065, filed Feb. 17, 2006, now U.S. Pat. No. 8,003,703 which is a National Stage application under 35 U.S.C. §371 and claims the benefit under 35 U.S.C. §119(a) of International Application No. PCT/GB2004/003551, having an International Filing Date of Aug. 18, 2004, which claims the benefit of priority of Swedish Application Serial Number 0302281-1, having a filing date of Aug. 21, 2003, and UK Application Serial Number 0412448.3, having a filing date of Jun. 4, 2004, all of which are incorporated herein in their entirety.

The present invention relates to substituted phenoxyacetic acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain phenoxyacetic acids are active at the CRTH2 receptor, and as a consequence are expected to be potentially useful for the treatment of various respiratory diseases, including asthma and COPD.

In a first aspect the invention therefore provides a method of treatment of human diseases or conditions in which modulation of CRTh2 receptor activity is beneficial, which comprises administering to a patient a compound of formula (I), or a pharmaceutically acceptable salt or solvate thereof:

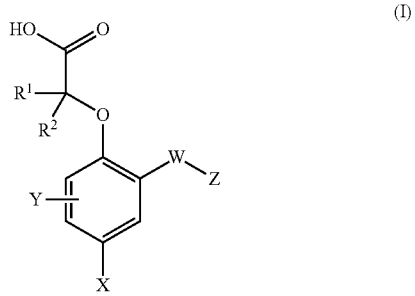

(I)

in which:
W is O, $S(O)_n$ (where n is 0, 1 or 2), $NR^{15}$, $CR^1R^2$ or $CR^1R^2$
X is hydrogen, halogen, cyano, nitro, $S(O)_n$ $R^6$, $OR^{12}$ or $C_{1-6}$alkyl which may be substituted by one or more halogen atoms;
Y is selected from hydrogen, halogen, CN, nitro, $SO_2R^3$, $OR^4$, $SR^4$, $SOR^3$, $SO_2NR^4R^5$, $CONR^4R^5$, $NR^4R^5$, $NR^6SO_2R^3$, $NR^6CO_2R^6$, $NR^6COR^3$, $C_2-C_6$ alkenyl, $C_2-C_6$ alkynyl, $C_3-C_7$ cycloalkyl or $C_{1-6}$alkyl, the latter four groups being optionally substituted by one or more substituents independently selected from halogen, $OR^6$ and $NR^6R^7$, $S(O)_nR^6$ where n is 0, 1 or 2;
Z is aryl or heteroaryl, optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, aryl, heteroaryl, $C_2-C_6$ alkenyl, $C_2-C_6$ alkynyl, $C_3-C_7$ cycloalkyl or $C_{1-6}$alkyl, the latter four groups being optionally substituted by one or more substituents independently selected from halogen, $C_3-C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$.

$R^1$ and $R^2$ independently represent a hydrogen atom, halogen, $C_2-C_6$ alkenyl, $C_2-C_6$ alkynyl, $C_3-C_7$ cycloalkyl or a $C_{1-6}$alkyl group, the latter four groups being optionally substituted by one or more substituents independently selected from halogen, $C_3-C_7$ cycloalkyl, $NR^6R^7$, $OR^6$, $S(O)_nR^6$ (where n is 0, 1 or 2);
or
$R^1$ and $R^2$ together can form a 3-8 membered ring optionally containing one or more atoms selected from O, S, $NR^6$ and itself optionally substituted by one or more $C_1-C_3$ alkyl or halogen;
$R^3$ represents $C_3-C_7$ cycloalkyl or $C_{1-6}$alkyl either of which may be optionally substituted by one or more substituents independently selected from halogen, $C_3-C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;
$R^4$ and $R^5$ independently represent hydrogen, $C_3-C_7$ cycloalkyl or $C_{1-6}$alkyl, the latter two groups being optionally substituted by one or more substituents independently selected from halogen, $C_3-C_7$ cycloalkyl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;
or
$R^4$ and $R^5$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_{1-3}$ alkyl;
$R^6$ and $R^7$ independently represents a hydrogen atom or $C_1-C_6$ alkyl;
$R^8$ is hydrogen, $C_{1-4}$ alkyl, —$COC_1-C_4$ alkyl, $CO_2C_1-C_4$alkyl, $SO_2R^6$ or $CONR^6C_1-C_4$alkyl;
$R^9$ represents aryl, heteroaryl, $C_3-C_7$ cycloalkyl or $C_{1-6}$alkyl, the latter two groups may be optionally substituted by one or more substituents independently selected from halogen, $C_3-C_7$ cycloalkyl, aryl, heteroaryl $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;
$R^{10}$ and $R^{11}$ independently represent aryl or heteroaryl, hydrogen, $C_3-C_7$ cycloalkyl or $C_{1-6}$ alkyl, the latter two groups being optionally substituted by one or more substituents independently selected from halogen, $C_3-C_7$ cycloalkyl, aryl, heteroaryl, $OR^6$ and $NR^6R^7$, $S(O)_nR^6$ (where n=0, 1 or 2), $CONR^6R^7$, $NR^6COR^7$, $SO_2NR^6R^7$ and $NR^6SO_2R^7$;
or
$R^{10}$ and $R^{11}$ together with the nitrogen atom to which they are attached can form a 3-8 membered saturated heterocylic ring optionally containing one or more atoms selected from O, $S(O)_n$ (where n=0, 1 or 2), $NR^8$, and itself optionally substituted by halogen or $C_1-C_3$ alkyl,
$R^{12}$ represents a hydrogen atom or $C_{1-6}$ alkyl which may be substituted by one or more halogen atoms, and
$R^{15}$ represents a hydrogen atom, $C_1-C_6$ alkyl, $SO_2R^6$ or $COR^6$.

Examples of aryl include phenyl and naphthyl.
Heteroaryl is defined as a 5-7 membered aromatic ring or can be a 6,6- or 6,5-fused bicyclic ring, all optionally containing one or more heteroatoms selected from N, S and O.
Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine and quinolone.

Aryl or heteroaryl groups can be optionally substituted by one or more substituents independently selected from hydrogen, halogen, CN, OH, SH, nitro, $CO_2R^6$, $SO_2R^9$, $OR^9$, $SR^9$, $SOR^9$, $SO_2NR^{10}R^{11}$, $CONR^{10}R^{11}$, $NR^{10}R^{11}$, $NHSO_2R^9$, $NR^9SO_2R^9$, $NR^6CO_2R^6$, $NHCOR^9$, $NR^9COR^9$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, $OR^6$, $NR^6R^7$, $S(O)_nR^6$ (where n is 0, 1 or 2), $CONR^6R^7$, $NR^6COR^7$, $SO_2NR^6R^7$ and $NR^6SO_2R^7$. Substituents can be present at any suitable position on the aryl and heteroaryl rings, including nitrogen atoms where appropriate.

In the context of the present specification, unless otherwise indicated, an alkyl or alkenyl group or an alkyl or alkenyl moiety in a substituent group may be linear or branched.

Heterocyclic rings as defined for $R^4$, $R^5$ and $R^{10}$ and $R^{11}$ means saturated heterocycles, examples include morpholine, azetidine, pyrrolidine, piperidine and piperazine.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably W is O, $S(O)_n$ (where n is 0, 1 or 2), $CR^1R^2$ or $NR^{15}$ where $R^{15}$ is hydrogen or methyl.

More preferably W is O, $CH_2$ or $NR^{15}$ where $R^{15}$ is hydrogen or methyl.

Even more preferably W is O, $CH_2$ or NH.

Most preferably W is O.

Preferably X is halogen, in particular fluoro and chloro, or $C_{1-2}$alkyl optionally substituted with one or more halogen atoms, such as $CF_3$.

More preferably X is fluoro, chloro or trifluoromethyl.

Even more preferably X is fluoro or chloro.

Preferably Y is hydrogen, halogen, in particular fluoro and chloro or $C_{1-6}$alkyl, such as methyl.

More preferably Y is hydrogen or halogen, in particular fluoro and chloro.

Even more preferably Y is hydrogen.

Preferably Z is phenyl, pyridyl or pyrimidyl, optionally substituted as defined above, more preferably Z is phenyl optionally substituted as defined above.

Preferred substituents for all Z groups include those substituents exemplified herein, in particular halogen, CN, $C_{1-3}$alkyl optionally substituted with one or more halogen atoms, $SO_2R^9$, $OR^9$, $SR^9$, $SOR^9$, $SO_2NR^{10}R^{11}$, $CONR^{10}R^{11}$, $NHSO_2R^9$, $NR^9SO_2R^9$, $NHCOR^9$ or $NR^9COR^9$. Preferably $R^9$ is methyl or ethyl.

More preferred substituents for all Z groups include halogen, in particular fluoro and chloro, $C_{1-3}$alkyl optionally substituted with one or more halogen atoms, $SO_2R^9$, $SO_2NR^{10}R^{11}$, $NHSO_2R^9$ or $NR^9SO_2R^9$.

Preferably Z is phenyl substituted by one or two substituents, preferably the substituent in the 4-position is selected from $SO_2R^9$, $SO_2NR^{10}R^{11}$, $NHSO_2R^9$ or $NR^9SO_2R^9$. Preferably $R^9$ is methyl or ethyl. Preferably $R^{10}$ and $R^{11}$ are both methyl.

Preferably Z is phenyl substituted by two substituents, preferably the substituent in the 4-position is selected from $SO_2R^9$, $SO_2NMe_2$, $NHSO_2R^9$ or $NR^9SO_2R^9$ where $R^9$ is methyl or ethyl and the substituent in the 2- or 3-position is selected from fluoro, chloro or $C_{1-3}$alkyl optionally substituted with one or more halogen atoms.

Preferably $R^1$ and $R^2$ are independently hydrogen or $C_{1-3}$ alkyl.

More preferably $R^1$ and $R^2$ are independently hydrogen or methyl.

Preferably when $R^1$ is alkyl and $R^2$ is hydrogen in the acid chain, the S-isomer is preferred Preferred compounds of formula (I) include those compounds exemplified herein, both in free base form as well as pharmaceutically acceptable salts and solvates thereof.

In a further aspect the invention provides a sub-set of compounds of formula (I), i.e. compounds of formula (IA) or pharmaceutically acceptable salts or solvates thereof:

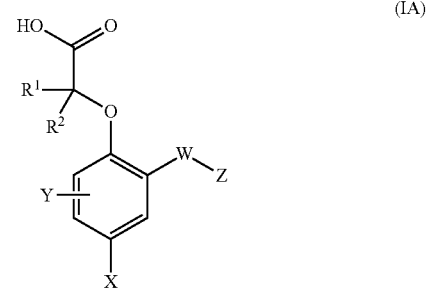

(IA)

in which:

W is O, $CH_2$, $S(O)_n$ (where n is 0, 1 or 2) or $NR^{15}$ where $R^{15}$ is hydrogen or methyl;

X is halogen or $C_{1-6}$alkyl which may be substituted by one or more halogen atoms;

Y is hydrogen, halogen or $C_{1-6}$alkyl;

Z is phenyl, pyridyl or pyrimidyl each optionally substituted by one or more substituents independently selected from halogen, CN, $C_{1-3}$alkyl optionally substituted with one or more halogen atoms, $SO_2R^9$, $OR^9$, $SR^9$, $SOR^9$, $SO_2NR^{10}R^{11}$, $CONR^{10}R^{11}$, $NHSO_2R^9$, $NR^9SO_2R^9$, $NHCOR^9$, $NR^9COR^9$;

$R^1$ and $R^2$ independently represent hydrogen or $C_{1-6}$alkyl;

$R^6$ and $R^7$ independently represent hydrogen atom or $C_{1-6}$alkyl;

$R^8$ is hydrogen, $C_{1-4}$ alkyl, —$COC_1$-$C_4$ alkyl, $CO_2C_1$-$C_4$alkyl, $SO_2R^6$ or $CONR^6C_1$-$C_4$alkyl;

$R^9$ is $C_{1-6}$alkyl optionally substituted by halogen, and $R^{10}$ and $R^{11}$ independently represent hydrogen or $C_{1-6}$alkyl, provided that:

the compounds 2-[4-methyl-2-(benzyl)phenoxy]acetic acid, 2-[4-chloro-2-(benzyl)phenoxy]propanopic acid, 2-[4-bromo-2-(4-chlorophenoxy)phenoxy]propanopic acid and 2-[4-chloro-2-(4-chlorophenoxy)phenoxy] propanopic acid are excluded;

when X is fluoro and W is S, then Z is not 5-fluoro-2-hydroxyphenyl, when X is chloro, Y is 3-methyl, $R^1$ and $R^2$ are both hydrogen and W is $CH_2$, then Z is not phenyl.

Suitably W is O, $CH_2$, $S(O)_n$ (where n is 0, 1 or 2) or $NR^{15}$ where $R^{15}$ is hydrogen or methyl. Preferably W is O, S, $CH_2$, NH or NMe, more preferably W is O, $CH_2$ or NH, even more preferably W is O or NH, most preferably W is O.

Preferably $R^1$ and $R^2$ are independently hydrogen or methyl. More preferably $R^1$ and $R^2$ are both hydrogen or one is hydrogen and the other is methyl.

Preferably X is halogen, in particular fluoro and chloro, or $C_{1-2}$ alkyl optionally substituted with one or more halogen atoms, such as $CF_3$.

More preferably X is fluoro, chloro or trifluoromethyl.
Even more preferably X is fluoro or chloro.
Preferably Y is hydrogen, halogen, in particular fluoro and chloro or $C_{1-6}$ alkyl, such as methyl.
More preferably Y is hydrogen or halogen, in particular fluoro and chloro.
Even more preferably Y is hydrogen.
Preferably Z is phenyl substituted by two substituents, preferably the substituent in the 4-position is selected from $SO_2R^9$, $SO_2NR^{10}R^{11}$, $NHSO_2R^9$ or $NR^9SO_2R^9$ and the substituent in the 2- or 3-position is selected from fluoro, chloro or $C_{1-3}$ alkyl optionally substituted with one or more halogen atoms. Preferably $R^9$ is methyl or ethyl. Preferably $R^{10}$ and $R^{11}$ are both methyl.

Preferred compounds of formula (IA) include:
[4-Chloro-2-[[4-(ethylsulfonyl)phenyl]thio]phenoxy]-acetic acid,
[4-Chloro-2-[[4-(ethylsulfonyl)-2-methylphenyl]thio]phenoxy]-acetic acid,
[4-Chloro-2-[4-(ethylsulfonyl)phenoxy]phenoxy]-acetic acid,
[4-Chloro-2-[[4-(methylsulfonyl)phenyl]amino]phenoxy]-acetic acid,
(4-Chloro-2-{[2-chloro-4-(methylsulfonyl)phenyl]thio}phenoxy)acetic acid,
(4-Chloro-2-{[2-chloro-4-(ethylsulfonyl)phenyl]thio}phenoxy)acetic acid,
(4-Chloro-2-{[4-(methylsulfonyl)phenyl]thio}phenoxy)acetic acid,
{4-Chloro-2-[(5-chloropyridin-2-yl)thio]phenoxy}acetic acid,
{4-Chloro-2-[(2-chloro-4-cyanophenyl)thio]phenoxy}acetic acid,
(4-Chloro-2-{[2-(methylsulfonyl)phenyl]thio}phenoxy)acetic acid,
(4-Chloro-2-{[4-(methylsulfonyl)phenyl]sulfinyl}phenoxy)acetic acid,
(4-Chloro-2-{[4-(methylsulfonyl)phenyl]sulfonyl}phenoxy)acetic acid,
[4-Chloro-2-({4-[(methylamino)carbonyl]phenyl}thio)phenoxy]acetic acid,
(2S)-2-(4-Chloro-2-{[4-(methylsulfonyl)phenyl]thio}phenoxy)propanoic acid,
(2R)-2-(4-Chloro-2-{[4-(methylsulfonyl)phenyl]thio}phenoxy)propanoic acid,
(2S)-2-(4-Chloro-2-{[2-chloro-4-(methylsulfonyl)phenyl]thio}phenoxy)propanoic acid,
(2S)-2-(4-Chloro-2-{[2-chloro-4-(ethylsulfonyl)phenyl]thio}phenoxy)propanoic acid,
2-(4-Chloro-2-{[2-chloro-4-(methylsulfonyl)phenyl]thio}phenoxy)-2-methylpropanoic acid,
{4-Chloro-2-[4-(methylsulfonyl)phenoxy]phenoxy}acetic acid,
{4-Chloro-2-[2-chloro-4-(methylsulfonyl)phenoxy]phenoxy}acetic acid,
{4-Chloro-2-[2-chloro-4-(ethylsulfonyl)phenoxy]phenoxy}acetic acid,
(2S)-2-{4-Chloro-2-[4-(methylsulfonyl)phenoxy]phenoxy}propanoic acid,
(2S)-2-{4-Chloro-2-[2-chloro-4-(methylsulfonyl)phenoxy]phenoxy}propanoic acid,
(2S)-2-{4-Chloro-2-[2-chloro-4-(ethylsulfonyl)phenoxy]phenoxy}propanoic acid,
{4,5-Dichloro-2-[2-chloro-4-(methylsulfonyl)phenoxy]phenoxy}acetic acid,
{2-[2-Chloro-4-(methylsulfonyl)phenoxy]-4,5-difluorophenoxy}acetic acid,
2-{4-Chloro-2-[2-chloro-4-(methylsulfonyl)phenoxy]phenoxy}-2-methylpropanoic acid,
(4-Chloro-2-{[2-chloro-4-(ethylsulfonyl)phenyl]amino}phenoxy)acetic acid,
(4-Chloro-2-{[2-chloro-4-(methylsulfonyl)phenyl]amino}phenoxy)acetic acid,
[2-{[2-Chloro-4-(methylsulfonyl)phenyl]thio}-4-(trifluoromethyl)phenoxy]acetic acid,
(2S)-2-[2-{[2-Chloro-4-(methylsulfonyl)phenyl]thio}-4-(trifluoromethyl)phenoxy]propanoic acid,
[2-{[2-Chloro-4-(ethylsulfonyl)phenyl]thio}-4-(trifluoromethyl)phenoxy]acetic acid,
(2S)-2-[2-{[2-Chloro-4-(ethylsulfonyl)phenyl]thio}-4-(trifluoromethyl)phenoxy]propanoic acid,
[2-({4-[(Dimethylamino)sulfonyl]phenyl}thio)-4-(trifluoromethyl)phenoxy]acetic acid,
[2-[2-Chloro-4-(methylsulfonyl)phenoxy]-4-(trifluoromethyl)phenoxy]acetic acid,
[2-[2-Chloro-4-(ethylsulfonyl)phenoxy]-4-(trifluoromethyl)phenoxy]acetic acid,
2-[2-[2-Chloro-4-(methylsulfonyl)phenoxy]-4-(trifluoromethyl)phenoxy]butanoic acid,
[2-{4-[(Dimethylamino)sulfonyl]phenoxy}-4-(trifluoromethyl)phenoxy]acetic acid,
(2S)-2-[2-{4-[(Dimethylamino)sulfonyl]phenoxy}-4-(trifluoromethyl)phenoxy]propanoic acid,
{2-[2-Chloro-4-(methylsulfonyl)phenoxy]-4-fluorophenoxy}acetic acid,
{2-[2-Chloro-4-(ethylsulfonyl)phenoxy]-4-fluorophenoxy}acetic acid,
2-{2-[2-Chloro-4-(methylsulfonyl)phenoxy]-4-fluorophenoxy}-2-methylpropanoic acid,
(2-{[2-chloro-4-(methylsulfonyl)phenyl]thio}-4-fluorophenoxy)acetic acid,
(2-{[2-Chloro-4-(ethylsulfonyl)phenyl]thio}-4-fluorophenoxy)acetic acid,
2-(2-{[2-Chloro-4-(methylsulfonyl)phenyl]thio}-4-fluorophenoxy)-2-methylpropanoic acid,
(2-{2-Chloro-4-[(ethylsulfonyl)amino]phenoxy}-4-fluorophenoxy)acetic acid,
(2S)-2-(4-Chloro-2-{[2-chloro-4-(ethylsulfonyl)phenyl]amino}phenoxy)propanoic acid,
2-(4-Chloro-2-{[2-chloro-4-(ethylsulfonyl)phenyl]amino}phenoxy)-2-methylpropanoic acid,
(2S)-2-(4-Chloro-2-{[2-chloro-4-(methylsulfonyl)phenyl]amino}phenoxy)propanoic acid,
2-(4-Chloro-2-{[2-chloro-4-(methylsulfonyl)phenyl]amino}phenoxy)-2-methylpropanoic acid,
[4-Chloro-2-(pyrimidin-5-yloxy)phenoxy]acetic acid,
[4-Chloro-2-(quinolin-3-yloxy)phenoxy]acetic acid,
(2-{[2-Chloro-4-(methylsulfonyl)phenyl]amino}-4-fluorophenoxy)acetic acid,
(2S)-2-(2-{[2-Chloro-4-(methylsulfonyl)phenyl]amino}-4-fluorophenoxy)propanoic acid,
{4-Chloro-2-[[2-chloro-4-(methylsulfonyl)phenyl](methyl)amino]phenoxy}acetic acid,
{4-Chloro-2-[[2-chloro-4-(methylsulfonyl)phenyl](ethyl)amino]phenoxy}acetic acid,
(2-{[2-Chloro-4-(ethylsulfonyl)phenyl]amino}-4-fluorophenoxy)acetic acid,
{2-[2-Chloro-4-(methylsulfonyl)phenoxy]phenoxy}acetic acid, {4-Chloro-2-[4-(methylsulfonyl)-3-(trifluoromethyl)phenoxy]phenoxy}acetic acid,

[4-Chloro-2-(quinolin-8-ylthio)phenoxy]acetic acid, (2S)-2-[4-Chloro-2-(4-nitrophenoxy)phenoxy]-propanoic acid, (2S)-2-(2-{[2-Chloro-4-(ethylsulfonyl)phenyl]amino}-4-fluorophenoxy)propanoic acid, 2-(2-{[2-Chloro-4-(ethylsulfonyl)phenyl]amino}-4-fluorophenoxy)-2-methylpropanoic acid,

[2-{[2-Chloro-4-(methylsulfonyl)phenyl]amino}-4-(trifluoromethyl)phenoxy]acetic acid,

[2-{[2-Chloro-4-(ethylsulfonyl)phenyl]amino}-4-(trifluoromethyl)phenoxy]acetic acid

[2-[4-(Ethylsulfonyl)benzyl]-4-(trifluoromethyl)phenoxy] acetic acid,

[4-Chloro-2-(3-cyanobenzyl)phenoxy]acetic acid, and pharmaceutically acceptable salts and solvates thereof.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, tert-butylamine, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by reaction of a compound of formula (II):

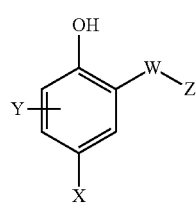

(II)

in which W, X, Y and Z are as defined in formula (I) or are protected derivatives thereof, with a compound of formula (III):

(III)

Where $R^1$ and $R^2$ are as defined in formula (I) or are protected derivatives thereof, $R^{13}$ is H or $C_1$-$C_{10}$ alkyl group and L is a leaving group, and optionally thereafter in any order:

removing any protecting group hydrolysing the ester group $R^{13}$ to the corresponding acid oxidation of sulphides to sulphoxides or sulphones forming a pharmaceutically acceptable salt.

The reaction can be carried out in a suitable solvent such as DMF using a base such as potassium carbonate or the like. Suitable groups $R^{13}$ include $C_{1-6}$ alkyl groups such as methyl, ethyl or tert-butyl. Suitable L is a leaving group such as halo, in particular chlorine or bromine L may also be hydroxy so that a Mitsunobu reaction may be performed with compound (II) using for example triphenylphosphine and diethyl azodicarboxylate.

Hydrolysis of the ester group $R^{13}$ can be carried out using routine procedures, for example treatment of methyl and ethyl esters with aqueous sodium hydroxide, and treatment of tert-butyl esters with acids such as trifluoroacetic acid.

Preferred intermediates of formula (II) include

4-Chloro-2-[[4-(ethylsulfonyl)-2-methylphenyl]thio]-phenol,

4-Chloro-2-{[2-chloro-4-(methylsulfonyl)phenyl]thio}phenol,

4-Chloro-2-{[2-chloro-4-(ethylsulfonyl)phenyl]thio}phenol,

4-Chloro-2-[2-chloro-4-(methylsulfonyl)phenoxy]phenol,

4-Chloro-2-[2-chloro-4-(ethylsulfonyl)phenoxy]phenol,

2-{[2-Chloro-4-(methylsulfonyl)phenyl]thio}-4-(trifluoromethyl)phenol,

2-{[2-Chloro-4-(methylsulfonyl)phenyl]thio}-4-fluorophenol,

4-Chloro-2-{[2-chloro-4-(ethylsulfonyl)phenyl]amino}phenol,

2-{[2-Chloro-4-(methylsulfonyl)phenyl]amino}-4-fluorophenol,

2-{[2-Chloro-4-(ethylsulfonyl)phenyl]amino}-4-fluorophenol,

2-{[2-Chloro-4-(methylsulfonyl)phenyl]amino}-4-(trifluoromethyl)phenol,

2-{[2-Chloro-4-(ethylsulfonyl)phenyl]amino}-4-(trifluoromethyl)phenol

Compounds of formula (II) can be prepared by reaction of a compound of formula (IV) with a compound of formula (V) followed by deprotection of $R^{14}$ when $R^{14}$ is not equal to H:

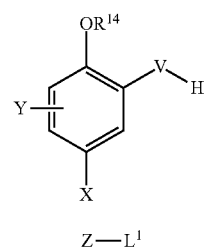

(IV)

Z—$L^1$ (V)

in which X, Y and Z are as defined in formula (I) or are protected derivatives thereof, V is S, $NR^6$ or O. $R^{14}$ is H or a suitable protecting group, for example benzyl, $L^1$ is iodide, bromide, chloride, fluoride or activated alcohol such as triflate.

The reaction can be carried out in a suitable solvent such as 1-methyl-2-pyrrolidinone with a base such as potassium carbonate, preferably at elevated temperatures. The reaction may also be catalysed with palladium or copper catalysts.

Preferred intermediates of formula (V) include

3-Chloro-4-fluorophenyl methyl sulfone,

3-Chloro-4-fluorophenyl ethyl sulfone

The sequence of the steps above may be changed, for example a compound of formula (VI) may be formed by the reaction of a compound of formula (VII) with a compound of formula (V).

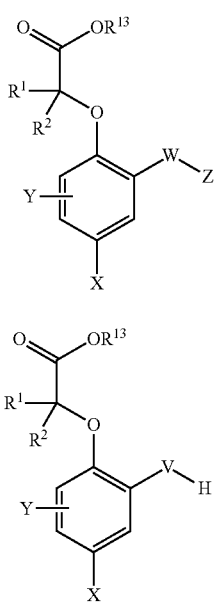

(VI)

(VII)

Preferred intermediates of formula (VII) include
2-(4-Chloro-2-hydroxyphenoxy)-2-methylpropanoic acid,
(4-Fluoro-2-hydroxyphenoxy)acetic acid,
2-(4-Fluoro-2-hydroxyphenoxy)-2-methylpropanoic acid,
(2S)-2-(4-Chloro-2-hydroxyphenoxy)propanoic acid Compounds of formula (I) can be prepared from a compound of formula (VIII) by formation of an organometallic (IX) followed by reaction with an electrophile such as (X) or (XI), then deprotection of $R^{14}$ as outlined in Scheme I.

Scheme 1

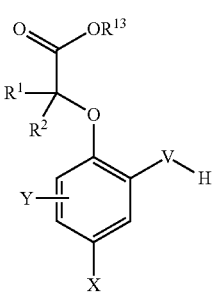

(VIII) (IX)

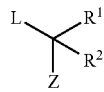

(II)

(X)

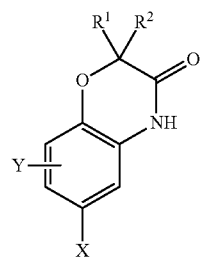

(XI)

in which X, Y are as defined in formula (I) or are protected derivatives thereof, W is defined as $CR^1R^2$ or $CR^1R^2$, $R^{13}$ is as defined in formula (IV), E is hydrogen or halogen and M is a metal such as Na or Li. For example when $R^{14}$ is benzyl and E is bromine, butyl lithium can be used to form the intermediate (IX) where M=Li. The reaction is performed at −78° C. in THF, then quenched with an electrophile such as (X) or (XI). When $R^2$=OH, this may be removed by reduction, for example hydrogenation with Pd/C. The protecting group $R^{14}$ may then be removed Compounds of formula (IV), where V=S can be prepared by reaction of a compound of formula (IX) with elemental sulphur.

Compounds of formula (I), where W=N can be prepared by reaction of a compound of formula (XII) with a compound of formula (V)

(XII)

in which X, Y, $R^1$ and $R^2$ are as defined in formula (I) or are protected derivatives thereof, The reaction can be carried out in a suitable solvent such as 1-methyl-2-pyrrolidinone with a base such as potassium carbonate, preferably at elevated temperatures.

Compounds of formula (II), where W=N can be prepared by reaction of a compound of formula (XIII) with a compound of formula (V).

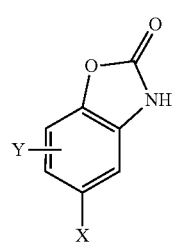

(XIII)

The reaction can be carried out in a suitable solvent such as 1-methyl-2-pyrrolidinone with a base such as potassium carbonate, preferably at elevated temperatures.

Compounds of formula (II), where W=C can be prepared by reaction of a compound of formula (XIV) with a compound of formula (XV)

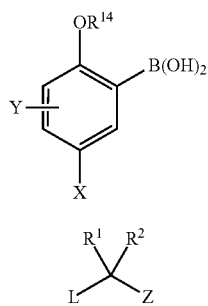

(XIV)

(XV)

in which X, Y, R¹, R², R¹⁴, Z and L are as defined as above or are protected derivatives thereof, The reaction can be carried out in a suitable solvent such as ethylene glycoldimethylether with a base such as sodium carbonate and a palladium catalyst, preferably at elevated temperatures.

Compounds of formula (I) and compound of formula (II), where can be prepared by reaction of a compound of formula (XVI) or a compound of formula (XVII) with a compound of formula (XVIII)

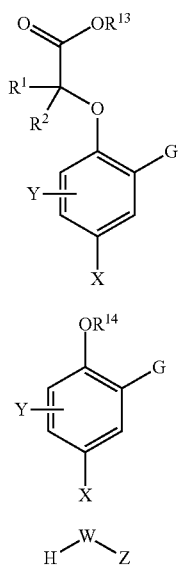

in which X, Y, R¹, R², R¹³, R¹⁴, Z and W are as defined as above or are protected derivatives thereof, G is halogen, triflate or boronic acid. The reaction can be carried out in a suitable solvent such as iso-propanol with a base such as potassium carbonate and a metal catalyst, such as copper, preferably at elevated temperatures.

In a further aspect, the present invention provides the use of a novel compound of formula (I)/(IA), and pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (respiratory tract)—obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (bone and joints) arthritides associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

(3) (skin) psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

(4) (eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(5) (gastrointestinal tract) glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema).

(6) (abdominal) hepatitis, including autoimmune, alcoholic and viral; fibrosis and cirrhosis of the liver; cholecystitis; pancreatitis, both acute and chronic.

(7) (genitourinary) nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

(8) (Allograft rejection) acute and chronic following, for example, transplantation of kidney, heart, liver, lung, bone marrow, skin or cornea or following blood transfusion; or chronic graft versus host disease;

(9) (CNS) Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes.

(10) Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome.

(11) Other disorders with an inflammatory or immunological component; including acquired immune deficiency syndrome (AIDS), leprosy, Sezary syndrome, and paraneoplastic syndromes.

(12) (Cardiovascular); atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; disorders of the proximal and peripheral veins including phlebitis and thrombosis, including deep vein thrombosis and complications of varicose veins.

(13) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

(14) Diseases associated with raised levels of $PGD_2$ or its metabolites.

Thus, the present invention provides a compound of formula (IA), or a pharmaceutically-acceptable salt or solvate thereof, as hereinbefore defined for use in therapy.

Preferably the compounds (I)/(IA) of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma or rhinitis.

In a further aspect, the present invention provides the use of a compound of formula (I)/(IA), or a pharmaceutically acceptable salt or solvate thereof, as hereinbefore defined in the manufacture of a medicament for use in therapy.

The invention further relates to combination therapies wherein a compound of formula (I)/(IA) or a pharmaceutically acceptable salt, solvate or in vivo hydrolysable ester thereof, or a pharmaceutical composition or formulation comprising a compound of formula (I)/(IA) is administered concurrently or sequentially or as a combined preparation with another therapeutic agent or agents, for the treatment of one or more of the conditions listed.

In particular, for the treatment of the inflammatory diseases rheumatoid arthritis, psoriasis, inflammatory bowel disease, COPD, asthma and allergic rhinitis the compounds of the invention may be combined with agents such as tumour necrosis factor alpha (TNF-α) inhibitors such as anti-TNF monoclonal antibodies (for example Remicade, CDP-870 and adalimumab) and TNF receptor immunoglobulin molecules (such as Enbrel); non-selective cyclo-oxygenase (COX)-1/COX-2 inhibitors whether applied topically or is systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes(LT)B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a phosphodiesterase (PDE) inhibitor such as the methylxanthanines including theophylline and aminophylline; and selective PDE isoenzyme inhibitors including PDE4 inhibitors and inhibitors of the isoform PDE4D, and inhibitors of PDES.

The present invention still further relates to the combination of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine, and mizolastine applied orally, topically or parenterally.

The present invention still further relates to the combination of a compound of the invention together with a gastroprotective histamine type 2 receptor antagonist.

The present invention still further relates to the combination of a compound of the invention with antagonists of the histamine type 4 receptor.

The present invention still further relates to the combination of a compound of the invention together with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

The present invention still further relates to the combination of a compound of the invention together with anticholinergic agents including muscarinic receptor (M1, M2, and M3) antagonists such as atropine, hyoscine, glycpyrrrolate, ipratropium bromide; tiotropium bromide; oxitropium bromide; pirenzepine; and telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present invention still further relates to the combination of a compound of the invention together with a chromone, including sodium cromoglycate and nedocromil sodium.

The present invention still further relates to the combination of a compound of the invention together with an insulin-like growth factor type I (IGF-1) mimetic.

The present invention still further relates to the combination of a compound of the invention together with an inhaled glucocorticoid, such as flunisolide, triamcinolone acetonide, beclomethasone dipropionate, budesonide, fluticasone propionate, ciclesonide, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the $C—X_3—C$ family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention still further relates to the combination of a compound of the invention together with other systemic or topically-applied anti-inflammatory agents including thalidomide and derivatives, retinoids, dithranol, and calcipotriol.

The present invention still further relates to the combination of a compound of the invention together with an antibacterial agent including penicillin derivatives, tetracyclines, macrolides, beta-lactams, fluoroquinolones, and inhaled aminoglycosides; and antiviral agents including acyclovir, famciclovir, valaciclovir, ganciclovir, cidofovir; amantadine, rimantadine; ribavirin; zanamavir and oseltamavir; protease inhibitors such as indinavir, nelfinavir, ritonavir, and saquinavir; nucleoside reverse transcriptase inhibitors such as didanosine, lamivudine, stavudine, zalcitabine, zidovudine; non-nucleoside reverse transcriptase inhibitors such as nevirapine, efavirenz.

The present invention still further relates to the combination of a compound of the invention together with cardiovascular agents such as calcium channel blockers, beta-adrenoceptor blockers, angiotensin-converting enzyme (ACE) inhibitors, angiotensin-2 receptor antagonists; lipid lowering agents such as statins, and fibrates; modulators of blood cell morphology such as pentoxyfylline; thrombolytics, and anticoagulants including platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with agents for the treatment of acute and chronic pain, including centrally and peripherally-acting analgesics such as opioid analogues and derivatives, carbamazepine, phenyloin, sodium valproate, amitryptiline and other antidepressant agents, and non-steroidal anti-inflammatory agents.

The present invention still further relates to the combination of a compound of the invention together with parenterally or topically-applied local anaesthetic agents such as lignocaine.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B_1$- and $B_2$.-receptor antagonists; (x)

anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ; (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK.sub1. and NK.sub3. receptor antagonists selected from the group consisting of NKP-608C; SB-233412 (talnetant); and D-4418; (xx) elastase inhibitors selected from the group consisting of UT-77 and ZD-0892; (xxi) TNF converting enzyme inhibitors (TACE); (xxii) induced nitric oxide synthase inhibitors (iNOS) or (xxiii) chemoattractant receptor-homologous molecule expressed on TH2 cells, (CRTH2 antagonists) (xxiv) inhibitors of P38

The compounds of the present invention may also be used in combination with anti-osteoporosis agents including hormonal agents such as raloxifene, and biphosphonates such as alendronate.

The compounds of the invention may also be used in combination with existing therapeutic agents for the treatment of osteoarthritis. Suitable agents to be used in combination include standard non-steroidal anti-inflammatory agents (hereinafter NSAIDs) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics, and intra-articular therapies such as corticosteroids and hyaluronic acid derivatives, and nutritional supplements such as glucosamine.

The compounds of the invention can also be used in combination with existing therapeutic agents for the treatment of cancer. Suitable agents to be used in combination include:
(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);
(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;
(iii) Agents which inhibit cancer cell invasion (for example metalloproteinase inhibitors like marimastat and inhibitors of urokinase plasminogen activator receptor function);
(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;
(v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);
(vi) vascular damaging agents such as combretastatin A4 and compounds disclosed in International Patent Applications WO 99/02166, WO00/40529, WO 00/41669, WO01/92224, WO02/04434 and WO02/08213;
(vii) antisense therapies, for example those which are directed to the targets listed above, such as ISIS 2503, an anti-ras antisense;
(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and
(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2 receptor), which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, and unless otherwise stated the mass ion quoted is the positive mass ion—(M+H)$^+$;

(iii) the title compounds of the examples and methods were named using the ACD/name (version 6.0) from Advanced Chemical Development Inc, Canada;

(iv) unless stated otherwise, reverse phase HPLC was conducted using a Symmetry, NovaPak or Ex-Terra reverse phase silica column;

(v) solvents were dried with MgSO$_4$ or Na$_2$SO$_4$ (vi) final compounds were prepared as the free acid or a suitable salt such as sodium (vii) the following abbreviations are used:
EtOAc Ethylacetate
DCM Dichloromethane
NMP N-methylpyrrolidine
DMF N,N-dimethylformamide
THF tetrahydrofuran
mcpba 3-chloroperoxybenzoic acid (Aldrich 77% max)

Pd(dppf)Cl$_2$ [1,1'-Bis(diphenylphosphino)ferrocene] dichloropalladium(II), complex with dichloromethane
RT room temperature

EXAMPLE 1

[4-Chloro-2-[[4-(ethylsulfonyl)phenyl]thio]phenoxy]-acetic acid, sodium salt

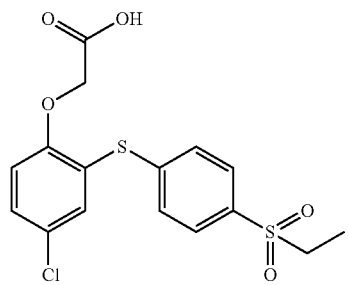 [SMILES: CCS(=O)(=O)c1ccc(Sc2cc(Cl)ccc2OCC(=O)O)cc1]

(i) 5-Chloro-2-methoxy-benzenethiol

Triphenylphosphine (11.4 g) was added portionwise to a stirred solution of 5-chloro-2-methoxybenzenesulphonyl chloride (3.0 g) in THF (30 ml). Water (4 ml) was added and the mixture stirred at RT for 2 h, afterwhich the reaction was diluted with water (25 ml) then 2M sodium hydroxide solution and washed with ether. The aqueous layer was acidified with 2M hydrochloric acid and extracted with ethylacetate. The organic layer was dried and evaporated under reduced pressure, yield 3.1 g.
MS: ESI (−ve) 173 (M−1)

(ii) 4-Chloro-2-[[4-(ethylsulfonyl)phenyl]thio]-1-methoxy-benzene

Potassium carbonate (0.315 g) was added to a stirred solution of the product from step (i) (0.4 g) and ethyl-(4-bromophenyl)-sulfone (0.285 g) in NMP (10 ml) and the mixture heated at 90° C. for 1 h. The mixture was partitioned between water/ethylacetate, the organics separated, dried, and evaporated under reduced pressure. The residue was purified by chromatography on silica eluting with 25% ethylacetate/isohexane. Yield 0.4 g
$^1$H NMR CDCl$_3$: δ 7.76-6.91 (7H, m); 3.81 (3H, s); 3.13-3.06 (2H, q); 1.30-1.22 (3H, t).

(iii)
4-Chloro-2-[[4-(ethylsulfonyl)phenyl]thio]-phenol

A solution of boron tribromide (1M in DCM, 2.3 ml) was slowly added to a stirred solution of the product from step (ii) (0.4 g) in DCM (20 ml) at 0° C. After 0.5 h a further 4 ml of boron tribromide solution was added and the mixture stirred for 1 h. The reaction was quenched with crushed ice and partitioned between water and DCM. The organics separated, dried, and evaporated under reduced pressure, yield 0.3 g.
MS: ESI (−ve) 327 (M−1)

(iv) [4-Chloro-2-[[4-(ethylsulfonyl)phenyl]thio]phenoxy]-acetic acid, 1,1-dimethylethyl ester A mixture of the product from step (iii) (0.3 g), tert-butyl-bromoacetate (0.15 ml) and potassium carbonate (0.13 g) in DMF (20 ml) was stirred at RT overnight. The mixture was partitioned between water and ethylacetate, the organics separated, dried, and evaporated under reduced pressure. Yield 0.55 g MS: ESI (+ve) 460 (M+NH$_4$)

(v) [4-Chloro-2-[[4-(ethylsulfonyl)phenyl]thio]phenoxy]-acetic acid, sodium salt Trifluoroacetic acid (10 ml) was added to a solution of the product from step (iv) (0.55 g) in DCM (10 ml) and the mixture stirred at RT for 1 h. The mixture was evaporated under reduced pressure and the residue purified by reverse phase HPLC. The sodium salt was made using sodium hydroxide, yield 0.21 g.

$^1$H NMR DMSO-d6: δ 7.74-7.71 (2H, m); 7.49-6.90 (4H, m); 6.90-6.88 (1H, d); 4.16 (2H, s); 3.26-3.22 (2H, q); 1.11-1.06 (3H, t).

MS: ESI (−ve) 385 (M−1)

EXAMPLE 2

[4-Chloro-2-[[4-(ethylsulfonyl)-2-methylphenyl]thio]phenoxy]-acetic acid, sodium salt

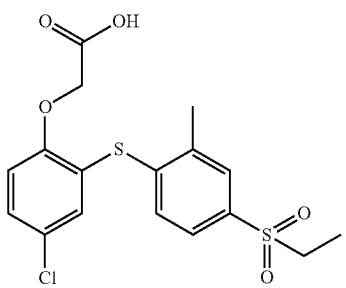 [SMILES: CCS(=O)(=O)c1ccc(Sc2cc(Cl)ccc2OCC(=O)O)c(C)c1]

(i) 1-Bromo-4-(ethylthio)-2-methyl-benzene

Bromine (2.2 ml) was added to a solution of 1-(ethylthio)-3-methylbenzene (6.6 g) in acetic acid (20 ml) at 0° C. The mixture was stirred at RT for 2 h then the solvent removed under reduced pressure. The residue was purified by chromatography on silica eluting with DCM. Yield 6.6 g MS: APCI (+ve): 247/9 (M+1)

(ii) 1-Bromo-4-(ethylsulfonyl)-2-methyl-benzene

3-Chloroperoxybenzoic acid (70% purity, 11.8 g) was added to a solution of the product from step (i) (5 g) in DCM (60 ml) and stirred at RT for 4 h. The mixture was partitioned between DCM/aq. sodium metabisulphite solution, the organics washed with aq. sodium hydrogencarbonate solution, water, dried and evaporated under reduced pressure. Yield 5.73 g $^1$H NMR CDCl$_3$: δ7.76-7.73 (2H, m); 7.58-7.56 (1H, m); 3.10 (2H, q); 2.49 (3H, s); 1.28 (3H, t)

(iii) 4-Chloro-2-[[4-(ethylsulfonyl)-2-methylphenyl]thio]-1-methoxy-benzene

The subtitle compound was prepared by the method of example 1 step (ii) using the product from step (ii). Yield 0.25 g $^1$H NMR CDCl$_3$ δ 7.70-6.91 (6H, m); 3.82 (3H, s); 3.13-3.06 (2H, q); 2.48 (3H, s); 1.30-1.22 (3H, t).

(iv) 4-Chloro-2-[[4-(ethylsulfonyl)-2-methylphenyl]thio]-phenol

The subtitle compound was prepared by the method of example 1 step (iii) using the product from step (iii). Yield 0.3 g MS: ESI (−ve) 341 (M−1)

(v) [4-Chloro-2-[[4-(ethylsulfonyl)-2-methylphenyl]thio]phenoxy]acetic acid-, 1,1-dimethylethyl ester The subtitle compound was prepared by the method of example 1 step (iv) using the product from step (iv). Yield 0.5 g MS: ESI (+ve) 474 (M+NH$_4$)

(vi) [4-Chloro-2-[[4-(ethylsulfonyl)-2-methylphenyl]thio]phenoxy]-acetic acid, sodium salt The title compound was prepared by the method of example 1 step (v) using the product from step (v). Yield 0.225 g $^1$H NMR DMSO-d6: δ 7.73-7.72 (1H, d) 7.55-7.52 (1H, dd); 7.41-7.38 (1H, dd); 7.27-7.21 (2H, m); 6.89-6.87 (1H, d); 4.14 (2H, s); 3.27-3.22 (2H, q); 2.42 (3H, s); 1.10-1.07 (3H, t).

MS: ESI (−ve) 399 (M−1)

EXAMPLE 3

[2-[[4-(Ethylsulfonyl)phenyl](hydroxy)methyl]-4-(trifluoromethyl)phenoxy]acetic acid

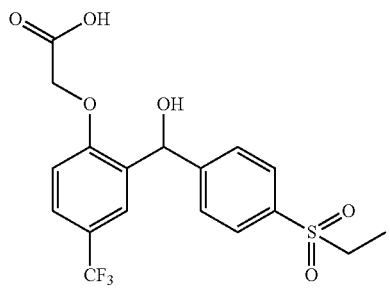 [SMILES: CCS(=O)(=O)c1ccc(C(O)c2cc(C(F)(F)F)ccc2OCC(=O)O)cc1]

(i) Benzyl 2-bromo-4-(trifluoromethyl)phenyl ether

Benzyl bromide (21.4 ml) was added to a stirred mixture of 2-bromo-4-trifluoromethylphenol (46.4 g) and potassium carbonate (39 g) in DMF (200 ml). After 18 h, the mixture was partitioned between diethylether and water, the organic layer washed with water, 2M sodium hydroxide solution, water, dried and the solvent evaporated under reduced pressure. Yield 58.7 g $^1$H NMR CDCl$_3$: δ 7.83 (1H, s); 7.51-7.32 (6H, m); 6.98 (1H, d); 5.21 (2H, s)

(ii) [2-(Benzyloxy)-5-(trifluoromethyl)phenyl][4-(ethylthio)phenyl]methanol

A solution of butyl lithium (1.6M in hexane, 1.03 ml) was added to a stirred solution of the product from step (i) (0.5 g)

in diethylether (20 ml) at −78° C. After 1 h, 4-ethylsulfanyl-benzaldehyde (0.25 g) was added and stirred for a further 1 h. The reaction was quenched with water, extracted with diethylether and the organic layer dried, then evaporated under reduced pressure. The residue was purified by chromatography on silica eluting with 50% diethylether/isohexane. Yield 0.7 g $^1$H NMR CDCl$_3$: δ 7.36-7.13 (12H, m); 6.04-6.03 (1H, d); 5.05 (2H, s); 2.96-2.89 (2H, q); 2.64-2.62 (1H, d); 1.33-1.28 (3H, t).

MS: ESI (+ve) 401 (M−OH)

(iii) [2-(Benzyloxy)-5-(trifluoromethyl)phenyl][4-(ethylsulfonyl)phenyl]methanol The subtitle compound was prepared by the method of example 2 step (ii) using the product from step (ii). Yield 0.45 g MS: ESI (+ve) 468 (M+NH$_4$)

(iv) 2-[[4-(Ethylsulfonyl)phenyl](hydroxy)methyl]-4-(trifluoromethyl)phenol

A mixture of the product from step (iii) (0.225 g), 10% palladium on carbon (0.05 g) in ethanol (20 ml) was hydrogenated at 1 Bar for 45 min. After filtration the solvent was evaporated under reduced pressure. Yield 0.22 g MS: ESI (−ve) 359 (M−H)

(v) [2-[[4-(Ethylsulfonyl)phenyl](hydroxy)methyl]-4-(trifluoromethyl)phenoxy]acetic acid The title compound was prepared by the method of example 1 steps (iv) and (v) using the is product from step (iv). Yield 0.045 g $^1$H NMR DMSO-d6: δ 7.80-7.52 (6H, m); 7.07-7.04 (1H, d); 6.12 (1H, s); 4.46 (2H, s); 3.41 (1H, bm); 3.27-3.20 (2H, q); 1.09-1.04 (3H, t).

MS: ESI (+ve) 436 (M+NH$_4$)

EXAMPLE 4

[2-[4-(Ethylsulfonyl)benzyl]-4-(trifluoromethyl)phenoxy]acetic acid

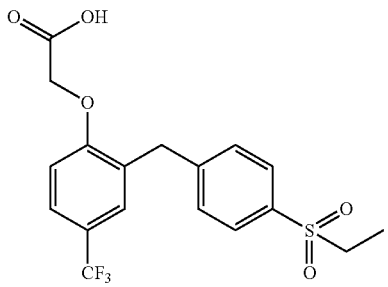 [SMILES: CCS(=O)(=O)c1ccc(Cc2cc(C(F)(F)F)ccc2OCC(=O)O)cc1]

(i) 2-[4-(Ethylsulfonyl)benzyl]-4-(trifluoromethyl)phenol

A mixture of the product from example 3 step (iii) (0.225 g), 10% palladium on carbon (0.05 g) and acetic acid (2 drops) in ethanol (20 ml) was hydrogenated at 3 Bar for 2 h then 5Bar for 5 h. After filtration the solvent was evaporated under reduced pressure. Yield 0.16 g MS: ESI (−ve) 343 (M−H)

(ii) [2-[4-(Ethylsulfonyl)benzyl]-4-(trifluoromethyl)phenoxy]acetic acid

The title compound was prepared by the method of example 1 steps (iv) and (v) using the product from step (i). Yield 0.11 g $^1$H NMR DMSO-d6: δ 7.75-7.46 (6H, m); 6.92-6.89 (1H, d); 4.21 (2H, s); 4.10 (2H, s); 3.31-3.19 (2H, q); 1.09-1.04 (3H, t).

MS: ESI (−ve) 401 (M−H)

EXAMPLE 5

[4-Chloro-2-[4-(ethylsulfonyl)phenoxy]phenoxy]acetic acid, sodium salt

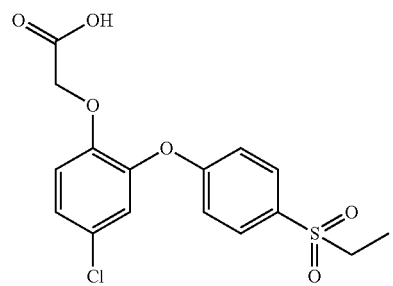 [SMILES: CCS(=O)(=O)c1ccc(Oc2cc(Cl)ccc2OCC(=O)O)cc1]

(i) (4-Chloro-2-methoxyphenoxy)-acetic acid, ethyl ester

The subtitle compound was prepared by the method of example 1 step (iv) using ethyl bromoacetate and 4-chloro-2-methoxyphenol Yield 2.7 g $^1$H NMR CDCl$_3$: δ 6.88-6.74 (3H, m); 4.64 (2H, s); 4.29-4.21 (2H, q); 3.88-3.87 (3H, s); 1.30-1.20 (3H, t).

(ii) (4-Chloro-2-hydroxyphenoxy)-acetic acid

A mixture of the product from step (i) (2.7 g) in 48% aqueous hydrogen bromide (30 ml) was heated under reflux for 2 h. The solvent was evaporated, the residue washed with water and dried, yield 1.7 g.

$^1$H NMR DMSO-d6: δ 6.89-6.72 (3H, m); 4.66 (2H, m); 3.79 (1H, s).

(iii) [4-Chloro-2-[4-(ethylsulfonyl)phenoxy]phenoxy]-acetic acid, sodium salt

Cesium carbonate (0.2 g) was added to a stirred mixture of the product from step (ii) (0.3 g), ethyl-(4-bromo-phenyl)-sulfone (0.37 g) and copper iodide (5 mol %) in NMP (20 ml) and the mixture heated at 170° C. (oil bath temp.) for 10 h. The mixture was quenched with 1M sodium hydroxide solution and extracted with ethylacetate. The aqueous layer was acidified with hydrochloric acid and extracted with ethylacetate. The organic extract was dried and evaporated under reduced pressure. The residue was purified by reverse phase HPLC, the sodium salt was formed using sodium hydroxide. Yield 0.068 g ¹H NMR DMSO-d6: δ 7.81-6.91 (7H, m); 4.06 (2H, s); 3.26-3.21 (2H, q); 1.11-1.08 (3H, t).
MS: ESI (−ve) 369 (M−H)

EXAMPLE 6

[4-Chloro-2-[[4-(methylsulfonyl)phenyl]amino]phenoxy]-acetic acid

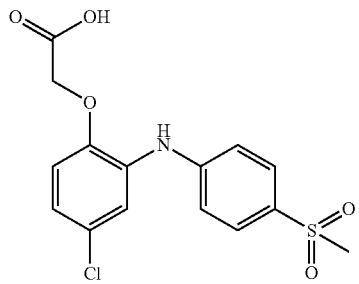 [SMILES: CS(=O)(=O)c1ccc(Nc2cc(Cl)ccc2OCC(=O)O)cc1]

(i) (4-Chloro-2-nitrophenoxy)-acetic acid, ethyl ester

The subtitle compound was prepared by the method of example 1 step (iv) using ethyl bromoacetate and 4-chloro-2-nitrophenol Yield 1.4 g (ii) 6-Chloro-2H-1,4-benzoxazin-3(4H)-one Iron powder (1.4 g) was added to a solution of the product from step (i) (1.4 g) in acetic acid (30 ml) and the mixture stirred at RT for 1 h. The mixture was filtered and the filtrate evaporated under reduced pressure. Yield 0.44 g
¹H NMR DMSO-d6: δ 8.43 (1H, m); 6.92-6.81 (3H, m); 4.61 (2H, s).

(iii) [4-Chloro-2-[[4-(methylsulfonyl)phenyl]amino]phenoxy]-acetic acid

Potassium carbonate (0.265 g) was added to a solution of the product from step (ii) (0.44 g) and 4-fluorophenyl methyl sulfone (0.331 g) in NMP (20 ml) and the mixture heated at 120° C. for 16 h. The reaction was diluted with water and extracted with ethylacetate, the organics were dried and evaporated under reduced pressure. The residue was purified by reverse phase HPLC, yield 0.096 g.
¹H NMR DMSO-d6: δ 11.33 (1H, s); 7.72-7.69 (2H, d); 7.31-7.30 (1H, m); 7.20-7.00 (3H, m); 6.92-6.89 (1H, d); 4.14 (2H, s); 3.11 (3H, s)
MS: APCI (+ve) 356 (M+H)

EXAMPLE 7

(4-Chloro-2-{[2-chloro-4-(methylsulfonyl)phenyl]thio}phenoxy)acetic acid

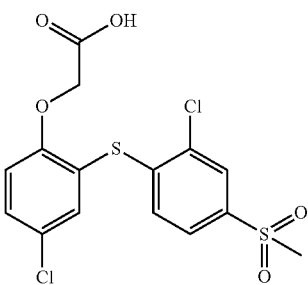 [SMILES: CS(=O)(=O)c1ccc(Sc2cc(Cl)ccc2OCC(=O)O)c(Cl)c1]

(i) 3-Chloro-4-fluorophenyl methyl sulfide

Iodomethane (1.15 ml) was added to a stirred mixture of 3-chloro-4-fluoro-benzenethiol (3.0 g), potassium carbonate (2.48 g) in DMF (20 ml) and left overnight. The reaction was diluted with water and extracted with diethylether, the organics were dried and evaporated under reduced pressure, yield 4.3 g.
1H NMR: CDCl₃: δ 7.31-7.14 (2H, m), 7.13-7.03 (1H, m), 3.23-3.21 (3H, s).

(ii) 3-Chloro-4-fluorophenyl methyl sulfone

The subtitle compound was prepared by the method of example 2 step (ii) using the product from step (i). Yield 3.8 g
1H NMR: CDCl₃: δ 8.06-8.03 (1H, m), 7.89-7.84 (1H, m), 7.38-7.32 (1H, m), 3.08 (3H, s).

(iii) 4-Chloro-2-{[2-chloro-4-(methylsulfonyl)phenyl]thio}phenol

The subtitle compound was prepared by the method of example 1 steps (i)-(iii) using the product from step (ii).
MS: ESI (−ve) 347 (M−1)

(iv) (4-Chloro-2-{[2-chloro-4-(methylsulfonyl)phenyl]thio}phenoxy)acetic acid

The title compound was prepared by the method of example 1 steps (iv)-(v) using the product from step (iii). Yield 0.158 g
1H NMR: DMSO-d6: δ 13.12 (1H, bs), 7.997-7.99 (1H, m), 7.69-7.58 (3H, m), 7.18-6.97 (2H, d), 4.80 (2H, s), 3.24 (3H, s).
MS: ESI (−ve) 406 (M−1)

EXAMPLE 8

(4-Chloro-2-{[2-chloro-4-(ethylsulfonyl)phenyl]thio}phenoxy)acetic acid, sodium salt

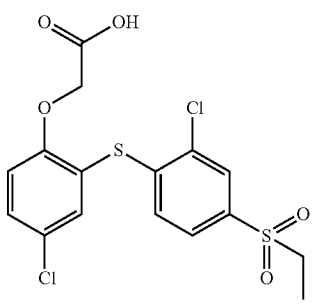 [SMILES: CCS(=O)(=O)c1ccc(Sc2cc(Cl)ccc2OCC(=O)O)c(Cl)c1]

(i) 3-Chloro-4-fluorophenyl ethyl sulfone

The subtitle compound was prepared by the method of example 7 step (i)-(ii) using iodoethane.
1H NMR: CDCl₃: δ 8.01-7.98 (1H, d), 7.84-7.79 (1H, m), 7.37-7.31 (1H, m), 3.17-3.09 (2H, q), 1.33-1.26 (3H, t).

(ii) 4-Chloro-2-{[2-chloro-4-(ethylsulfonyl)phenyl]thio}phenol

The subtitle compound was prepared by the method of example 1 steps (i)-(iii) using the product from step (i).
MS: ESI (−ve) 362 (M−1)

(iii) (4-Chloro-2-{[2-chloro-4-(ethylsulfonyl)phenyl]thio}phenoxy)acetic acid, sodium salt The title compound was prepared by the method of example 1 steps (iv)-(v) using the product from step (ii), yield 0.19 g.

1H NMR: DMSO-d6: δ 7.90-7.89 (1H, d), 7.61-7.58 (1H, d), 7.53-7.49 (2H, m), 7.29-7.27 (1H, d), 6.95-6.92 (1H, d), 4.17 (2H, s), 3.34-3.30 (2H, m), 1.14-1.08 (3H, m).

MS: ESI (−ve) 420 (M−1)

EXAMPLE 9

(4-Chloro-2-{[4-(methylsulfonyl)phenyl]thio}phenoxy)acetic acid

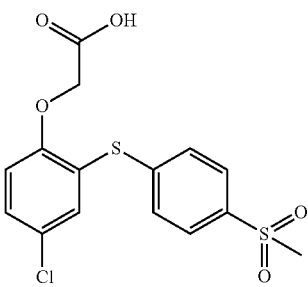 [SMILES: CS(=O)(=O)c1ccc(Sc2cc(Cl)ccc2OCC(=O)O)cc1]

(i) 4-Chloro-2-{[4-(methylsulfonyl)phenyl]thio}phenol

The subtitle compound was prepared by the method of example 1 steps (i)-(iii) using methyl-(4-bromo-phenyl)sulphone, yield 0.98 g.

MS: ESI (−ve) 313 (M−1)

(ii) tert-Butyl (4-chloro-2-{[4-(methylsulfonyl)phenyl]thio}phenoxy)acetate

The subtitle compound was prepared by the method of example 1 step (iv) using the product from step (i), yield 0.95 g.

MS: ESI (+ve) 443 (M+NH₄)

(iii) (4-Chloro-2-{[4-(methylsulfonyl)phenyl]thio}phenoxy)acetic acid

The title compound was prepared by the method of example 1 step (v) using the product from step (ii), yield 0.165 g.

1H NMR: DMSO-d6: δ 7.80-7.77 (2H, m), 7.47-7.41 (3H, m), 7.38-7.37 (1H, d), 6.93-6.91 (1H, d), 4.27 (2H, s), 3.19 (3H, s).

MS: ESI (−ve) 371 (M−1)

EXAMPLE 10

{4-Chloro-2-[(5-chloropyridin-2-yl)thio]phenoxy}acetic acid

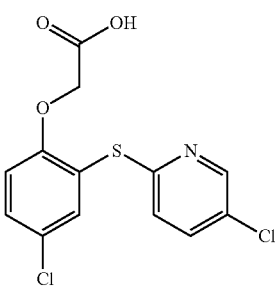 [SMILES: O=C(O)COc1ccc(Cl)cc1Sc1ccc(Cl)cn1]

The title compound was prepared by the general method of example 1.

1H NMR: DMSO-d6: δ 8.46-8.45 (1H, m), 7.76-7.73 (1H, d), 7.59-7.58 (1H, d), 7.52-7.50 (1H, d), 7.10-7.04 (2H, m), 4.74 (2H, s).

MS: ESI (−ve) 329 (M−1)

EXAMPLE 11

{4-Chloro-2-[(2-chloro-4-cyanophenyl)thio]phenoxy}acetic acid

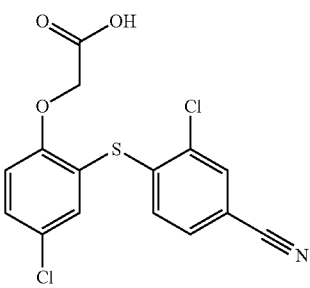 [SMILES: N#Cc1ccc(Sc2cc(Cl)ccc2OCC(=O)O)c(Cl)c1]

The title compound was prepared by the general method of example 1.

1H NMR: DMSO-d6: δ 8.07 (1H, d), 7.62-7.57 (3H, m), 7.16-7.12 (1H, m), 6.90-6.87 (1H, d), 4.75 (2H, s).

MS: ESI (−ve) 353 (M−1)

EXAMPLE 12

(4-Chloro-2-{[2-(methylsulfonyl)phenyl]thio}phenoxy)acetic acid

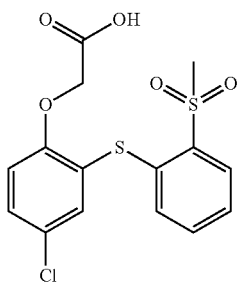 [SMILES: CS(=O)(=O)c1ccccc1Sc1cc(Cl)ccc1OCC(=O)O]

The title compound was prepared by the general method of example 1.

1H NMR: DMSO-d6: δ 13.05 (1H, bs), 7.94-7.92 (1H, d), 7.60-7.42 (4H, m), 7.42-7.08 (2H, m), 4.67 (2H, s), 3.44 (3H, s).

MS: ESI (−ve) 371 (M−1)

EXAMPLE 13

(4-Chloro-2-{[4-(methylsulfonyl)phenyl]sulfinyl}phenoxy)acetic acid, sodium salt

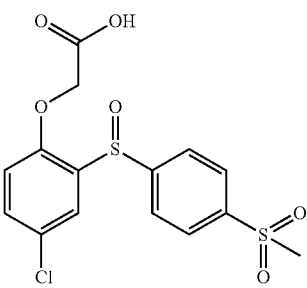 [SMILES: CS(=O)(=O)c1ccc(S(=O)c2cc(Cl)ccc2OCC(=O)O)cc1]

(i) tert-Butyl (4-chloro-2-{[4-(methylsulfonyl)phenyl]sulfinyl}phenoxy)acetate 3-Chloroperoxybenzoic acid (70% purity, 0.2 g) was added to a solution of the product from example 9 step (ii) (0.35 g) in DCM (10 ml) and stirred at 0° C. for 1 h. The mixture was partitioned between DCM/aq. sodium metabisulphite solution, the organics washed with aq. sodium hydrogencarbonate solution, water, dried and evaporated under reduced pressure. Yield 0.34 g MS: APCI (−ve) 388 (M-tert-butyl)

(ii) (4-Chloro-2-{[4-(methylsulfonyl)phenyl]sulfinyl}phenoxy)acetic acid, sodium salt The title compound was prepared by the method of example 1 step (v) using the product from step (i), yield 0.071 g.

1H NMR: DMSO-d6: δ 8.33-8.31 (2H, d), 8.01-7.99 (2H, d), 7.56-7.55 (1H, d), 7.45-7.42 (1H, d), 6.95-6.93 (1H, d), 4.30-4.22 (2H, q), 3.24 (3H, s).
MS: APCI (+ve) 389 (M+1)

EXAMPLE 14

(4-Chloro-2-{[4-(methylsulfonyl)phenyl]sulfonyl}phenoxy)acetic acid

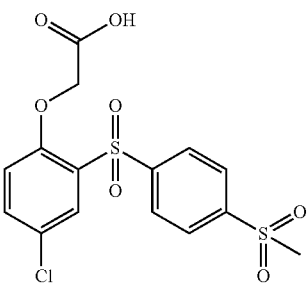 [SMILES: CS(=O)(=O)c1ccc(S(=O)(=O)c2cc(Cl)ccc2OCC(=O)O)cc1]

(i) tert-Butyl (4-chloro-2-{[4-(methylsulfonyl)phenyl]sulfonyl}phenoxy)acetate 3-Chloroperoxybenzoic acid (70% purity, 0.4 g) was added to a solution of the product from example 9 step (ii) (0.35 g) in DCM (10 ml) and stirred at 0° C. for 1 h. The mixture was partitioned between DCM/aq. sodium metabisulphite solution, the organics washed with aq. sodium hydrogencarbonate solution, water, dried and evaporated under reduced pressure. Yield 0.36 g

(ii) (4-Chloro-2-{[4-(methylsulfonyl)phenyl]sulfonyl}phenoxy)acetic acid

The title compound was prepared by the method of example 1 step (v) using the product from step (i), yield 0.108 g.

1H NMR: DMSO-d6: δ 8.35-8.32 (2H, d), 8.10-8.06 (2H, d), 7.96-7.95 (1H, d), 7.71-7.68 (1H, d), 7.08-7.06 (1H, d), 4.46 (2H, s), 3.27 (3H, s).
MS: ESI (−ve) 403 (M−1)

EXAMPLE 15

[4-Chloro-2-({4-[(methylamino)carbonyl]phenyl}thio)phenoxy]acetic acid

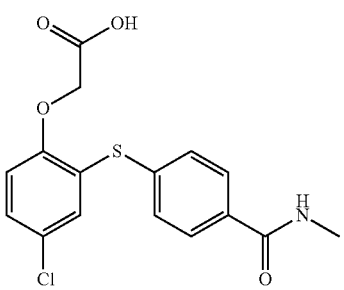 [SMILES: CNC(=O)c1ccc(Sc2cc(Cl)ccc2OCC(=O)O)cc1]

(i) Ethyl 4-[(5-chloro-2-methoxyphenyl)thio]benzoate

A mixture of the product from example 1 step (i) (0.5 g), ethyl-4-fluoro-benzoate (0.32 ml), 25% wt potassium fluoride on alumina (1.25 g) and 18-crown-6 (8 mg) in DMSO (20 ml) was heated at 140° C. for 4 h. The mixture was cooled, diluted with ethylacetate (100 ml), filtered and the filtrate washed with water, brine, dried and evaporated under reduced pressure. The residue was purified by chromatography on silica eluting with DCM/isohexane (2:1), yield 0.24 g.

MS: ESI (+ve) 323 (M+1)

(ii) 4-[(5-Chloro-2-methoxyphenyl)thio]benzoic acid

A mixture of the product from step (i) (0.24 g), lithium hydroxide (0.036 g) in methanol (30 ml) and water (5 ml) was stirred at RT overnight then acidified with 2M hydrochloric acid. The mixture was extracted with ethylacetate, the organics dried and evaporated under reduced pressure, yield 0.23 g MS: ESI (−ve) 293 (M−1)

(iii) 4-[(5-Chloro-2-methoxyphenyl)thio]-N-methylbenzamide

A mixture of the product from step (ii) (0.23 g), 1-(3-dimethylaminopropyl)-3-ethylcarbodiimide hydrochloride (0.22 g), 1-hydroxybenzotriazole (0.15 g), N,N-diisopropylethylamine (0.3 g) and methylamine (2M in THF, 0.78 ml) in DMF (10 ml) was stirred at RT overnight. Water was added and the mixture extracted with ethylacetate, the organics were dried and evaporated under reduced pressure, yield 0.24 g.

MS: ESI (+ve) 308 (M+1)

(iv) [4-Chloro-2-({4-[(methylamino)carbonyl]phenyl}thio)phenoxy]acetic acid The title compound was prepared by the method of example 1 steps (iii)-(v) using the product from step (iii), yield 0.119 g.

1H NMR: DMSO-d6: δ 13.12 (1H, bs), 8.47-8.46 (1H, m), 7.82-7.80 (2H, m), 7.40-7.34 (3H, m), 7.04-7.01 (2H, m), 4.78 (2H, s), 2.66 (3H, s).

MS: ESI (−ve) 350 (M−1)

EXAMPLE 16

(2S)-2-(4-Chloro-2-{[4-(methylsulfonyl)phenyl]thio}phenoxy)propanoic acid

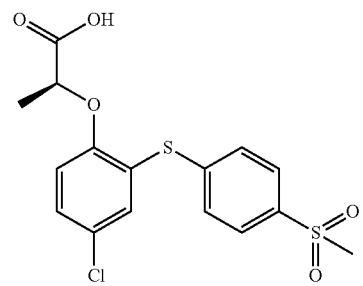 [SMILES: C[C@H](Oc1ccc(Cl)cc1Sc1ccc(S(C)(=O)=O)cc1)C(=O)O]

(i) tert-Butyl (2S)-2-(4-chloro-2-{[4-(methylsulfonyl)phenyl]thio}phenoxy) propanoate Diisopropyl azodicarboxylate (0.19 ml) was added to a stirred solution of the product from example 9 step (i) (0.3 g), triphenylphosphine (0.25 g), R-tert-butyl lactate (0.14 g) in THF (10 ml). After 2 h the solvent was evaporated under reduced pressure and the residue purified by chromatography on silica eluting with diethylether/isohexane (2:1), yield 0.6 g.

MS: ESI (+ve) 460 (M+NH4)

(ii) (2S)-2-(4-Chloro-2-{[4-(methylsulfonyl)phenyl]thio}phenoxy)propanoic acid

The title compound was prepared by the method of example 1 step (v) using the product from step (i), yield 0.15 g.

1H NMR: DMSO-d6: δ 7.82-7.80 (2H, m), 7.46-7.39 (4H, m), 6.95-6.93 (1H, d), 4.66-4.64 (1H, m), 3.18 (3H, s), 1.25-1.23 (3H, d).

MS: ESI (−ve) 385 (M−1)

EXAMPLE 17

(2R)-2-(4-Chloro-2-{[4-(methylsulfonyl)phenyl]thio}phenoxy)propanoic acid

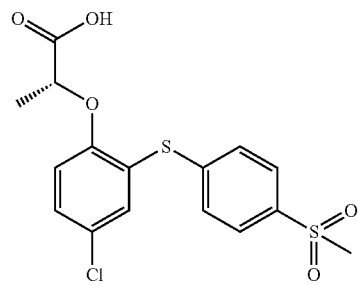 [SMILES: C[C@@H](Oc1ccc(Cl)cc1Sc1ccc(S(C)(=O)=O)cc1)C(=O)O]

(i) Methyl (2R)-2-(4-chloro-2-{[4-(methylsulfonyl)phenyl]thio}phenoxy)propanoate The subtitle compound was prepared by the method of example 16 step (i) using S-methyl lactate, yield 0.35 g.

MS: ESI (+ve) 418 (M+NH4)

(ii) (2R)-2-(4-Chloro-2-{[4-(methylsulfonyl)phenyl]thio}phenoxy)propanoic acid

The title compound was prepared by the method of example 15 step (ii) using the product from step (i), yield 0.13 g.

1H NMR: DMSO-d6: δ 7.82-7.79 (2H, m), 7.47-7.40 (4H, m), 6.96-6.94 (1H, d), 4.70-4.67 (1H, q), 3.18 (3H, s), 1.26-1.12 (3H, d).

MS: ESI (−ve) 385 (M−1)

EXAMPLE 18

(2S)-2-(4-Chloro-2-{[2-chloro-4-(methylsulfonyl)phenyl]thio}phenoxy)propanoic acid, sodium salt

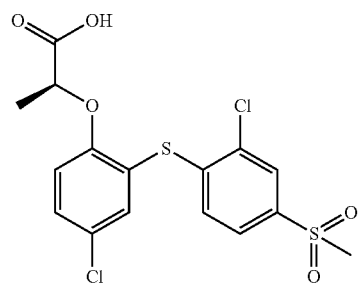 [SMILES: C[C@H](Oc1ccc(Cl)cc1Sc1ccc(S(C)(=O)=O)cc1Cl)C(=O)O]

The title compound was prepared by the method of example 16 using the product from example 7 step (iii), yield 0.2 g.

1H NMR: DMSO-d6: δ 7.96-7.95 (1H, m), 7.67-7.63 (1H, m), 7.49-7.45 (2H, m), 7.35-7.32 (1H, m), 6.93-6.90 (1H, d), 4.27-4.20 (1H, q), 3.23 (3H, s), 1.17-1.06 (3H, d).

MS: ESI (−ve) 419/421 (M−1)

EXAMPLE 19

(2S)-2-(4-Chloro-2-{[2-chloro-4-(ethylsulfonyl)phenyl]thio}phenoxy)propanoic acid, sodium salt

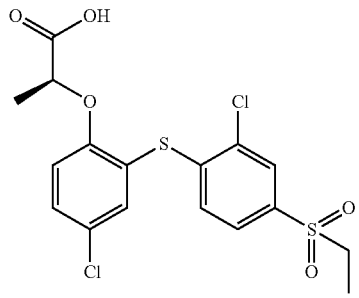 [SMILES: CCS(=O)(=O)c1ccc(Sc2cc(Cl)ccc2O[C@@H](C)C(=O)O)c(Cl)c1]

The title compound was prepared by the method of example 16 using the product from example 8 step (ii), yield 0.54 g.

1H NMR: DMSO-d6: δ 7.90-7.89 (1H, m), 7.62-7.47 (3H, m), 7.30-7.28 (1H, d), 6.95-6.92 (1H, d), 4.35-4.32 (1H, q), 3.39-3.29 (2H, q), 1.13-1.05 (6H, d+t).

MS: ESI (−ve) 433 (M−1)

EXAMPLE 20

2-(4-Chloro-2-{[2-chloro-4-(methylsulfonyl)phenyl]thio}phenoxy)-2-methylpropanoic acid

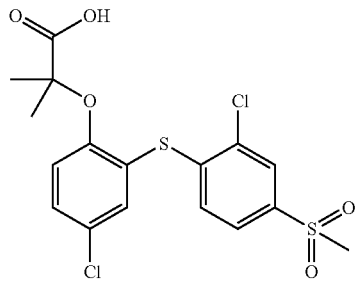

The title compound was prepared by the method of example 1 step (iv) using the product from example 7 step (iii) and tert-butyl-2-bromoisobutyrate, yield 0.028 g.

1H NMR: DMSO-d6: δ 8.02-8.01 (1H, m), 7.73-7.69 (1H, m), 7.56-7.50 (2H, m), 7.12-6.95 (2H, d), 3.25 (3H, s), 1.33 (6H, s).

MS: ESI (−ve) 433/435 (M−1)

EXAMPLE 21

{4-Chloro-2-[4-(methylsulfonyl)phenoxy]phenoxy}acetic acid, sodium salt

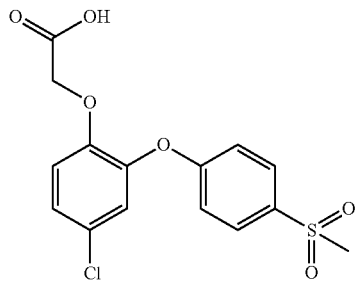 [SMILES: CS(=O)(=O)c1ccc(Oc2cc(Cl)ccc2OCC(=O)O)cc1]

A mixture of the product from example 5 step (ii) (0.3 g), methyl-(4-fluoro-phenyl)sulfone (0.226 g) and potassium carbonate (0.18 g) in NMP (20 ml) was heated at 160° C. for 2 h. The mixture was partitioned between ethylacetate/2M hydrochloric acid, the organics separated, dried, and evaporated under reduced pressure. The residue was purified by reverse phase HPLC, the sodium salt formed from sodium hydroxide. Yield 0.103 g 1H NMR DMSO-d6: δ 7.85-7.80 (1H, d), 7.25-7.14 (5H, d), 6.95-6.91 (1H, d), 4.10 (2H, s), 3.17 (3H, s).

MS: ESI (−ve) 355 (M−1)

EXAMPLE 22

{4-Chloro-2-[2-chloro-4-(methylsulfonyl)phenoxy]phenoxy}acetic acid, sodium salt

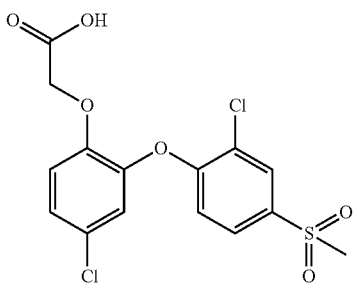 [SMILES: CS(=O)(=O)c1ccc(Oc2cc(Cl)ccc2OCC(=O)O)c(Cl)c1]

The title compound was prepared by the method of example 21 using the product from example 5 step (ii) and example 7 step (ii), yield 0.132 g.

1H NMR: DMSO-d6: δ 8.05-8.04 (1H, m), 7.73-7.71 (1H, m), 7.28-7.25 (2H, m), 7.18-7.16 (1H, m), 6.96-6.94 (1H, m), 4.11 (2H, s), 3.24 (3H, s).

MS: ESI (−ve) 389 (M−1)

EXAMPLE 23

{4-Chloro-2-[2-chloro-4-(ethylsulfonyl)phenoxy]phenoxy}acetic acid

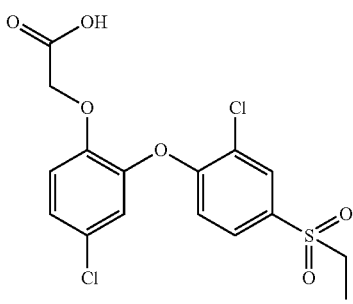 [SMILES: CCS(=O)(=O)c1ccc(Oc2cc(Cl)ccc2OCC(=O)O)c(Cl)c1]

The title compound was prepared by the method of example 21 using the product from example 5 step (ii) and example 8 step (i), yield 0.296 g.

1H NMR: DMSO-d6: δ 8.00-7.99 (1H, d), 7.72-7.68 (1H, m), 7.34-7.32 (2H, m), 7.07-7.04 (2H, d), 4.41 (2H, s), 3.39-3.29 (2H, q), 1.15-1.07 (3H, t).

MS: ESI (−ve) 403/405 (M−1)

EXAMPLE 24

(2S)-2-{4-Chloro-2-[4-(methylsulfonyl)phenoxy]phenoxy}propanoic acid, sodium salt

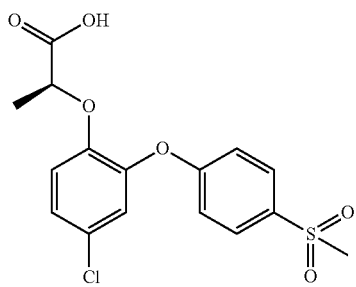 [SMILES: C[C@H](Oc1ccc(Cl)cc1Oc1ccc(S(C)(=O)=O)cc1)C(=O)O]

(i) 4-Chloro-1-methoxy-2-[4-(methylsulfonyl)phenoxy]benzene

The subtitle compound was prepared by the method of example 1 step (ii) using 5-chloro-2-methoxy-phenol, yield 0.35 g.
1H NMR: CDCl$_3$: δ 7.88-7.85 (2H, d), 7.27-6.95 (5H, m), 3.78 (3H, s), 3.06-3.05 (3H, s).

(ii) 4-Chloro-2-[4-(methylsulfonyl)phenoxy]phenol

The subtitle compound was prepared by the method of example 1 step (iii) using the product from step (i), yield 0.17 g.
MS: APCI (−ve) 297 (M−1)

(iii) (2S)-2-{4-Chloro-2-[4-(methylsulfonyl)phenoxy]phenoxy}propanoic acid, sodium salt The title compound was prepared by the method of example 16 using the product from step (ii), yield 0.063 g.
1H NMR: DMSO-d6: δ 7.85-7.80 (2H, m), 7.22-7.16 (4H, m), 6.93-6.90 (1H, d), 4.19-4.12 (1H, q), 3.14 (3H, s), 1.11-1.06 (3H, d).
MS: ESI (−ve) 369 (M−1)

EXAMPLE 25

(2S)-2-{4-Chloro-2-[2-chloro-4-(methylsulfonyl)phenoxy]phenoxy}propanoic acid

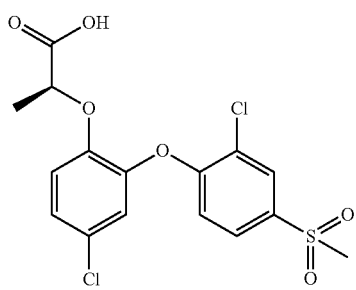 [SMILES: C[C@H](Oc1ccc(Cl)cc1Oc1ccc(S(C)(=O)=O)cc1Cl)C(=O)O]

(i) 3-Chloro-4-(5-chloro-2-methoxyphenoxy)phenyl methyl sulfone

The subtitle compound was prepared by the method of example 1 step (ii) using the product from example 7 step (ii) and 5-chloro-2-methoxy phenol. Yield 4.0 g
MS: ESI (+ve) 363 (M+NH$_4$)

(ii) 4-Chloro-2-[2-chloro-4-(methylsulfonyl)phenoxy]phenol

The subtitle compound was prepared by the method of example 1 step (iii) using the product from step (i). Yield 3.0 g
MS: ESI (−ve) 331 (M−1)

(iii) (2S)-2-{4-Chloro-2-[2-chloro-4-(methylsulfonyl)phenoxy]phenoxy}propanoic acid The title compound was prepared by the method of example 16 using the product from step (ii). Yield 0.206 g
1H NMR: DMSO-d6: δ 8.09-8.08 (1H, m), 7.78-7.75 (1H, m), 7.39-7.32 (2H, m), 7.09-7.07 (1H, d), 7.00-6.98 (1H, d), 4.87-4.80 (1H, q), 3.24 (3H, s), 1.25-1.15 (3H, d).
MS: ESI (−ve) 403/405 (M−1)

EXAMPLE 26

(2S)-2-{4-Chloro-2-[2-chloro-4-(ethylsulfonyl)phenoxy]phenoxy}propanoic acid

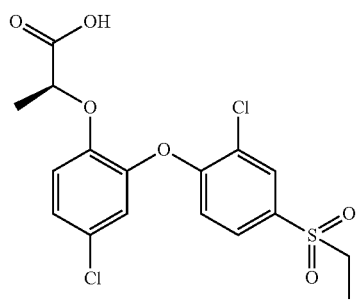 [SMILES: CCS(=O)(=O)c1ccc(Oc2cc(Cl)ccc2O[C@@H](C)C(=O)O)c(Cl)c1]

(i) 4-Chloro-2-[2-chloro-4-(ethylsulfonyl)phenoxy]-1-methoxybenzene

The subtitle compound was prepared by the method of example 1 step (ii) using the is product from example 8 step (i) and 5-chloro-2-methoxy phenol. Yield 3.30 g
MS: ESI (+ve) 378 (M+NH$_4$)

(ii) 4-Chloro-2-[2-chloro-4-(ethylsulfonyl)phenoxy]phenol

The subtitle compound was prepared by the method of example 1 step (iii) using the product from step (i). Yield 3.10 g
MS: ESI (−ve) 345 (M−1)

(iii) Methyl (2S)-2-{4-chloro-2-[2-chloro-4-(ethylsulfonyl)phenoxy]phenoxy}propanoate The subtitle compound was prepared by the method of example 16 step (i) using the product from step (ii) and R-methyl lactate. Yield 2.30 g
MS: ESI (+ve) 435 (M+NH$_4$)

(iv) (2S)-2-{4-Chloro-2-[2-chloro-4-(ethylsulfonyl) phenoxy]phenoxy}propanoic acid A mixture of the product from step (iii) (2.3 g) and lithium hydroxide (0.303 g) in water (10 ml) and THF (10 ml) was stirred at RT for 1 h. The mixture was diluted with water, extracted with diethylether then the aqueous layer acidified by 2M hydrochloric acid and extracted with ethylacetate. The ethyl acetate layer was dried, evaporated under reduced pressure and the residue purified by RPHPLC.

1H NMR: DMSO-d6: δ 7.99-7.67 (2H, m), 7.33-6.95 (4H, m), 4.36-4.34 (1H, q), 3.35-3.29 (2H, q), 1.25-1.15 (6H, m).
MS: ESI (−ve) 417/419 (M−1)

EXAMPLE 27

{4,5-Dichloro-2-[2-chloro-4-(methylsulfonyl)phenoxy]phenoxy}acetic acid

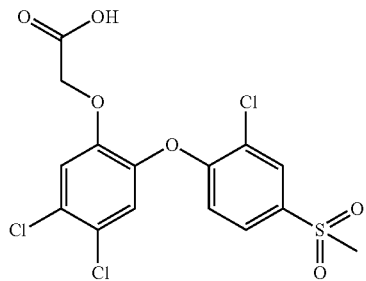 [SMILES: CS(=O)(=O)c1ccc(Oc2cc(Cl)c(Cl)cc2OCC(=O)O)c(Cl)c1]

A mixture of sodium hydride (60% wt. disp. in oil, 0.223 g) and 4,5-dichlorocatechol (1 g) in DMF (10 ml) was stirred at RT for 15 min. tert-Butyl-bromoacetate (0.9 ml) was added, stirred at RT for 2 h then potassium carbonate (0.77 g) and the product from example 7 step (ii) (0.7 g) added and the mixture heated at 90° C. for 14 h. The mixture was partitioned between 2M sodium hydroxide solution and diethylether, the aqueous layer was acidified with 2M hydrochloric acid and extracted with ethylacetate. The ethylacetate layer was dried, evaporated under reduced pressure and the residue purified by RPHPLC. Yield 0.349 g.

1H NMR: DMSO-d6: δ 8.06-7.71 (2H, m), 7.54 (1H, s), 7.27-7.13 (2H, m), 4.32. (2H, s), 3.24 (3H, s).
MS: ESI (−ve) 423/425 (M−1)

EXAMPLE 28

{2-[2-Chloro-4-(methylsulfonyl)phenoxy]-4,5-difluorophenoxy}acetic acid

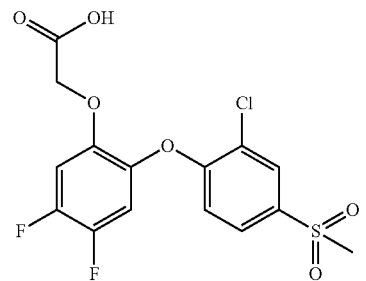 [SMILES: CS(=O)(=O)c1ccc(Oc2cc(F)c(F)cc2OCC(=O)O)c(Cl)c1]

(i) 4,5-Difluoro-2-methoxyphenol

Sodium thiomethoxide (0.4 g) was added to a solution of 1,2-difluoro-4,5-dimethoxybenzene (1.0 g) in DMF (10 ml) at RT, then heated at 100° C. for 4 h. A further 0.8 g of sodium thiomethoxide was added, the mixture heated for a further 2 h. The mixture was cooled, partitioned between ethylacetate/2M hydrochloric acid, the organics dried and evaporated under reduced pressure, yield 1.05 g

(ii) tert-Butyl (4,5-difluoro-2-methoxyphenoxy)acetate

The subtitle compound was prepared by the method of example 1 step (iv) using the product from step (i), yield 0.75 g.

1H NMR: CDCl$_3$: δ 6.76-6.70 (2H, m), 4.51 (2H, s), 3.84 (3H, s), 1.48 (9H, s).

(iii) (4,5-Difluoro-2-hydroxyphenoxy)acetic acid

A mixture of the product from step (ii) (0.75 g) and lithium chloride (0.345 g) in DMF (20 ml) was heated at 150° C. for 6 h, cooled and partitioned between ethylacetate/2M hydrochloric acid. The organics were dried and evaporated under reduced pressure, yield 0.7 g.

(iv) {2-[2-Chloro-4-(methylsulfonyl)phenoxy]-4,5-difluorophenoxy}acetic acid A mixture of sodium hydride (60% wt. disp. in oil, 0.275 g) and the product from step (iii) (0.7 g) in DMF (10 ml) was stirred at RT for 15 min. The product from example 7 step (ii) (0.715 g) was added and the mixture heated at 85° C. for 15 h. The mixture was partitioned between 2M sodium hydroxide solution and diethylether, the aqueous layer was acidified with 2M hydrochloric acid and extracted with ethylacetate. The ethylacetate layer was dried, evaporated under reduced pressure and the residue purified by RPHPLC. Yield 0.076 g.

1H NMR: DMSO-d6: δ 8.07 (1H, s), 7.76-7.73 (1H, m), 7.59-7.54 (1H, m), 7.43-7.38 (1H, m), 6.98-6.96 (1H, m), 4.69 (2H, s), 3.24 (3H, s).
MS: ESI (−ve) 391 (M−1)

EXAMPLE 29

2-{4-Chloro-2-[2-chloro-4-(methylsulfonyl)phenoxy]phenoxy}-2-methylpropanoic acid

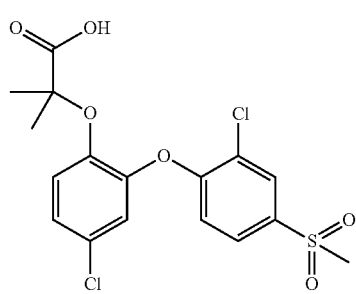 [SMILES: CC(C)(Oc1ccc(Cl)cc1Oc1ccc(S(C)(=O)=O)cc1Cl)C(=O)O]

(i) 2-(Benzyloxy)-4-chlorophenol

Sulfuryl chloride (0.965 ml) was added to a stirred solution of 2-(benzyloxy)phenol (2.0 g) in dry toluene (20 ml) at 0° C.

The mixture was warmed to RT and stirred overnight then cooled to 0° C. and quenched with ice-water before extracting with ethylacetate. The organics were dried, evaporated under reduced pressure and the residue purified by chromatography on silica eluting with DCM/isohexane (1:1). Yield 1.5 g MS: ESI (−ve) 233 (M−1)

(ii) 2-[2-(Benzyloxy)-4-chlorophenoxy]-2-methyl-propanoic acid

Powdered sodium hydroxide (0.253 g) was added to a stirred mixture of the product from step (i) (1.5 g) and 1,1,1-trichloro-2-methylpropanol (3.0 g) in acetone (40 ml) at 0° C. After stirring at RT for 1 h the mixture was cooled to 0° C. and a further portion of sodium hydroxide (0.253 g) added. After repeating for a third time, the mixture was stirred at RT overnight, then quenched with 2M hydrochloric acid and extracted with ethylacetate. The organics were dried, evaporated under reduced pressure and the residue purified by chromatography on silica eluting with diethylether:isohexane (1:1). Yield 1.4 g

(iii) 2-(4-Chloro-2-hydroxyphenoxy)-2-methylpropanoic acid

A mixture of the product from step (ii) (1.4 g) and 10% Pd/C (0.14 g) in ethylacetate (30 ml) was hydrogenated at 2 Bar for 3 h then filtered through celite. The filtrate was evaporated under reduced pressure, yield 0.6 g.

MS: ESI (−ve) 229 (M−1)

(iv) 2-{4-Chloro-2-[2-chloro-4-(methylsulfonyl)phenoxy]phenoxy}-2-methylpropanoic acid The title compound was prepared by the method of example 28 step (iv) using the product from step (iii). Yield 0.039 g 1H NMR: DMSO-d6: δ 8.08-8.07 (1H, s), 7.78-7.75 (1H, m), 7.39-7.39 (1H, m), 7.28-7.25 (1H, m), 7.06-6.98 (2H, m), 3.24 (3H, s), 1.22 (6H, s).

MS: ESI (−ve) 417 (M−1)

EXAMPLE 30

(4-Chloro-2-{[2-chloro-4-(ethylsulfonyl)phenyl]amino}phenoxy)acetic acid

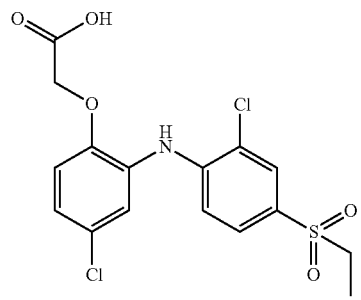

A mixture of the product from example 8 step (i) (0.21 g), 6-chloro-2H-1,4-benzoxazin-3(4H)-one (0.15 g) and potassium carbonate (0.23 g) in DMF was heated in a microwave (CEM, 50 W) at 120° C. for 5 min. The mixture was heated at 140° C. for a further 5 min, cooled and partitioned between ethylacetate/2M hydrochloric acid. The organics were separated, washed with brine, dried and evaporated under reduced pressure. The residue was purified by RPHPLC, yield 0.08 g.

1H NMR: DMSO-d6: δ 8.82 (1H, s), 7.78 (1H, s), 7.57 (1H, d), 7.33 (1H, s), 7.17 (1H, d), 7.10 (1H, d), 7.07 (1H, d), 4.51 (2H, s), 3.24 (2H, q), 1.10 (3H, t)

MS: APCI (−ve) 402 (M−1)

EXAMPLE 31

(4-Chloro-2-{[2-chloro-4-(methylsulfonyl)phenyl]amino}phenoxy)acetic acid

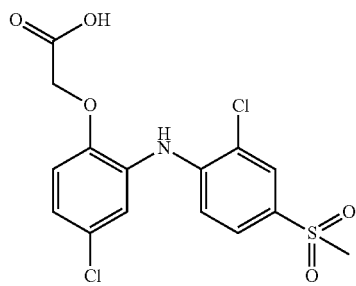 [SMILES: CS(=O)(=O)c1ccc(Nc2cc(Cl)ccc2OCC(=O)O)c(Cl)c1]

The title compound was prepared by the method of example 30 using the product from example 7 step (ii). Yield 1.54 g $^1$H NMR: DMSO-d6: δ 13.14 (1H, s), 7.94 (1H, s), 7.87 (1H, s), 7.61 (1H, d), 7.35 (1H, s), 7.22 (1H, d), 7.09 (1H, d), 6.99 (1H, d), 4.77 (2H, s), 3.18 (3H, s)

MS: APCI (+ve) 391 (M+1)

EXAMPLE 32

[2-{[2-Chloro-4-(methylsulfonyl)phenyl]thio}-4-(trifluoromethyl)phenoxy]acetic acid

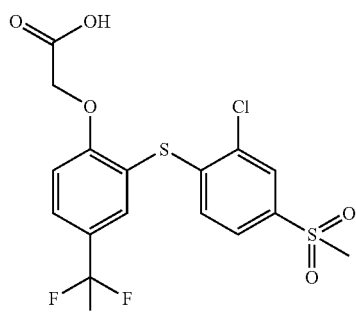

(i) 2-(Benzyloxy)-5-(trifluoromethyl)benzenethiol

A solution of butyllithium (1.6M in hexanes, 18.5 ml) was added dropwise to a stirred solution of 2-(benzyloxy)-5-trifluoromethylthiophenol (7.0 g) in dry diethylether (40 ml) at −78° C. After 40 min elemental sulphur (0.68 g) was added, the mixture was stirred at −78 C for 1 h, quenched with 2M NaOH solution and extracted with diethylether. The aqueous layer was acidified, extracted with ethyl acetate, the ethyl acetate layer dried and evaporated under reduced pressure. The residue was purified by chromatography on silica eluting with diethylether:isohexane 1:6, yield 4.40 g.

MS: ESI (−ve) 283 (M−1)

(ii) 4-{[2-(Benzyloxy)-5-(trifluoromethyl)phenyl]thio}-3-chlorophenyl methyl sulfone The subtitle compound was prepared by the method of example 1 step (ii) using the product from step (i) and the product from example 7 step (ii), yield 0.43 g.

1H NMR: CDCl$_3$: δ 7.89-6.81 (11H, m), 5.13 (2H, s), 3.00 (3H, s).

(iii) 2-{[2-Chloro-4-(methylsulfonyl)phenyl]thio}-4-(trifluoromethyl)phenol

The subtitle compound was prepared by the method of example 1 step (iii) using the product from step (ii), yield 0.22 g.

MS: ESI (−ve) 381/383 (M−1)

(iv) [2-{[2-Chloro-4-(methylsulfonyl)phenyl]thio}-4-(trifluoromethyl)phenoxy]acetic acid The title compound was prepared by the method of example 1 steps (iv-v) using the product from step (iii), yield 0.054 g.

1H NMR: DMSO-d6: δ 7.998-7.99 (1H, s), 7.90-7.88 (2H, m), 7.67-7.65 (1H, d), 7.28-7.26 (1H, d), 7.03-7.01 (1H, d), 4.77 (2H, s), 3.23 (3H, s).

MS: ESI (−ve) 438 (M−1)

EXAMPLE 33

(2S)-2-[2-{[2-Chloro-4-(methylsulfonyl)phenyl]thio}-4-(trifluoromethyl)phenoxy]propanoic acid, sodium salt

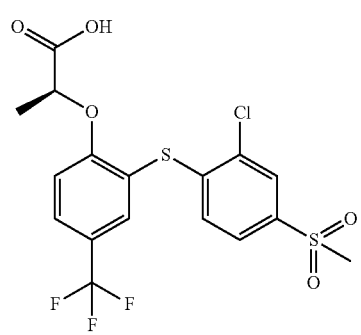 [SMILES: C[C@H](Oc1ccc(C(F)(F)F)cc1Sc1ccc(S(C)(=O)=O)cc1Cl)C(=O)O]

The title compound was prepared by the method of example 16 using the product from example 32 step (iii).

1H NMR: DMSO-d6: δ 7.97 (1H, s), 7.82-7.80 (2H, m), 7.66-7.65 (1H, m), 7.31-7.28 (1H, d), 7.10-7.07 (1H, d), 4.54-4.49 (1H, q), 2.99 (3H, s), 1.20-1.18 (3H, d).

MS: ESI (−ve) 453 (M−1)

EXAMPLE 34

[2-{[2-Chloro-4-(ethylsulfonyl)phenyl]thio}-4-(trifluoromethyl)phenoxy]acetic acid, sodium salt

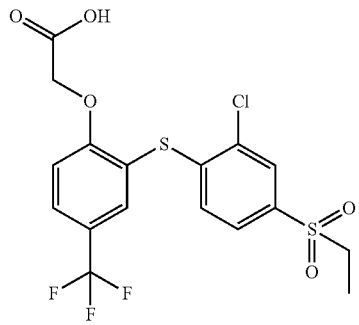 [SMILES: CCS(=O)(=O)c1ccc(Sc2cc(C(F)(F)F)ccc2OCC(=O)O)c(Cl)c1]

The title compound was prepared by the method of example 32 using the product from example 8 step (i).

1H NMR: DMSO-d6: δ 7.90-7.81 (3H, m), 7.59-7.56 (1H, d), 7.30-7.27 (1H, d), 7.10-7.08 (1H, d), 4.27 (2H, s), 3.39-3.29 (2H, q), 1.10-1.07 (3H, t).

MS: ESI (−ve) 453 (M−1)

EXAMPLE 35

(2S)-2-[2-{[2-Chloro-4-(ethylsulfonyl)phenyl]thio}-4-(trifluoromethyl)phenoxy]propanoic acid, sodium salt

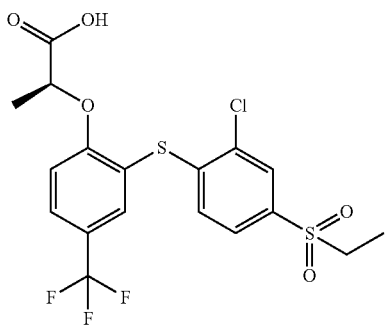 [SMILES: CCS(=O)(=O)c1ccc(Sc2cc(C(F)(F)F)ccc2O[C@@H](C)C(=O)O)c(Cl)c1]

The title compound was prepared by the method of example 16 and example 32.

1H NMR: DMSO-d6: δ 7.90-7.78 (3H, m), 7.60-7.57 (1H, m), 7.37-7.35 (1H, d), 7.06-7.04 (1H, d), 4.37-4.35 (1H, q), 3.34-3.29 (2H, q), 1.14-1.05 (6H, d+t).

MS: ESI (−ve) 467 (M−1)

EXAMPLE 36

[2-{4-[(Dimethylamino)sulfonyl]phenyl}thio)-4-(trifluoromethyl)phenoxy]acetic acid, sodium salt

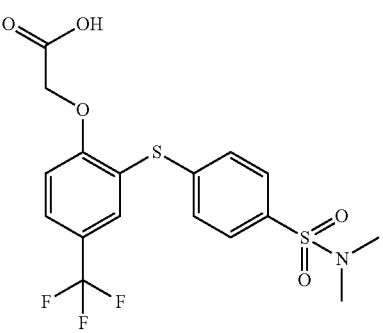

(i) 4-Fluoro-N,N-dimethylbenzenesulfonamide

Dimethylamine hydrochloride (1.27 g) was added to a solution of 4-fluoro-benzenesulphonyl chloride (3.0 g) and N,N-diisopropylethylamine (5.37 ml) in dichloromethane (30 ml), the mixture was stirred at RT for 1 h, diluted with water, extracted with dichloromethane, dried and evaporated under reduced, yield 3.0 g.

(ii) [2-({4-[(Dimethylamino)sulfonyl]phenyl}thio)-4-(trifluoromethyl)phenoxy]acetic acid, sodium salt The title compound was prepared by the method of example 32 using the product from step (i).
1H NMR: DMSO-d6: δ 7.73-7.71 (1H, m), 7.62-7.60 (3H, m), 7.51-7.49 (2H, d), 7.04-7.02 (1H, d), 4.25 (2H, s), 2.58 (6H, s).
MS: ESI (−ve) 434 (M−1)

EXAMPLE 37

[2-[2-Chloro-4-(methylsulfonyl)phenoxy]-4-(trifluoromethyl)phenoxy]acetic acid

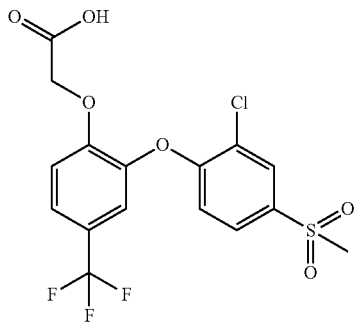 [SMILES: CS(=O)(=O)c1ccc(Oc2cc(C(F)(F)F)ccc2OCC(=O)O)c(Cl)c1]

(i) Benzyl 2-fluoro-5-(trifluoromethyl)phenyl ether

A mixture of 5-(trifluoromethyl)-2-fluorophenol (2.0 g), benzyl bromide (1.45 ml) and potassium carbonate (1.65 g) in dry DMF (20 ml) was stirred at RT overnight. The mixture was quenched with water and the solid filtered and dried, yield 2.20 g.
1H NMR: CDCl$_3$: δ 7.47-7.14 (8H, m), 5.16 (2H, s).

(ii) 2-(Benzyloxy)-1-methoxy-4-(trifluoromethyl)benzene

A solution of sodium methoxide in methanol (25% wt, 20 ml) and the product from step (i) (1.20 g) was heated at 100° C. for 3 h. The mixture was quenched with water (100 ml) and the solid was filtered and dried, yield 1.28 g.
1H NMR: CDCl$_3$: δ 7.46-6.91 (8H, m), 5.15 (2H, s), 3.19 (3H, s).

(iii) 2-Methoxy-5-(trifluoromethyl)phenol

The subtitle compound was prepared by the method of example 29 step (iii) using the product from step (ii), yield 0.70 g.
MS: ESI (−ve) 191 (M−1)

(iv) [2-[2-Chloro-4-(methylsulfonyl)phenoxy]-4-(trifluoromethyl)phenoxy]acetic acid The title compound was prepared by the method of example 1 steps (ii-v) using the product from step (iii).
1H NMR: DMSO-d6: δ 8.08 (1H, m), 7.77-7.65 (3H, m), 7.33-7.30 (1H, d), 6.95-6.92 (1H, d), 4.79 (2H, s), 3.25 (3H, s).
MS: ESI (−ve) 423 (M−1)

EXAMPLE 38

[2-[2-Chloro-4-(ethylsulfonyl)phenoxy]-4-(trifluoromethyl)phenoxy]acetic acid

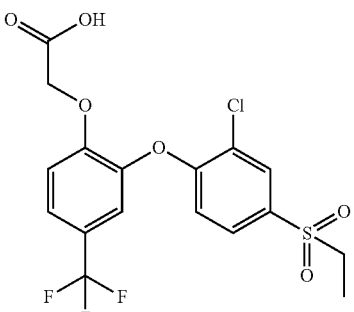

The title compound was prepared by the method of example 37 using the product from example 8 step (i).
1H NMR: DMSO-d6: δ 7.99 (1H, s), 7.68-7.54 (3H, m), 7.20-7.18 (1H, d), 7.11-7.09 (1H, d), 4.20 (2H, s), 3.35-3.30 (2H, q), 1.12-1.08 (3H, t).
MS: ESI (−ve) 437 (M−1)

EXAMPLE 39

2-[2-[2-Chloro-4-(methylsulfonyl)phenoxy]-4-(trifluoromethyl)phenoxy]butanoic acid, sodium salt

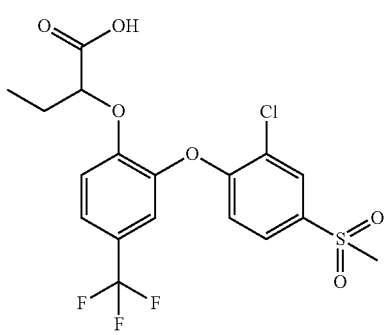 [SMILES: CCC(Oc1ccc(C(F)(F)F)cc1Oc1ccc(S(C)(=O)=O)cc1Cl)C(=O)O]

The title compound was prepared by the method of example 37 using ethyl-2-butyrate.
$^1$H NMR: DMSO-d6: δ 8.05-8.04 (1H, s), 7.71-7.68 (1H, m), 7.57-7.56 (2H, m), 7.17-7.15 (1H, d), 7.05-7.03 (1H, d), 4.14-4.11 (1H, t), 3.20 (3H, s), 1.59-1.52 (2H, m), 0.52-0.49 (3H, t).
MS: ESI (−ve) 451 (M−1)

EXAMPLE 40

[2-{4-[(Dimethylamino)sulfonyl]phenoxy}-4-(trifluoromethyl)phenoxy]acetic acid, sodium salt

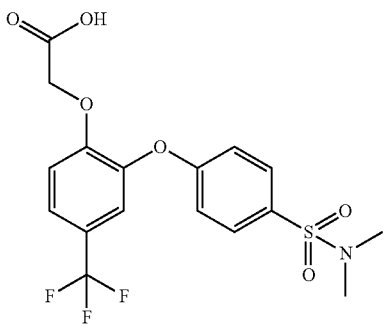 [SMILES: CN(C)S(=O)(=O)c1ccc(Oc2cc(C(F)(F)F)ccc2OCC(=O)O)cc1]

(i) 4-[2-Hydroxy-5-(trifluoromethyl)phenoxy]-N,N-dimethylbenzenesulfonamide

The subtitle compound was prepared by the method of example 1 steps (ii-iii) using the products from example 37 step (iii) and example 36 step (i), yield 0.95 g.
MS: ESI (−ve) 360 (M−1).

(ii) [2-{4-[(Dimethylamino)sulfonyl]phenoxy}-4-(trifluoromethyl)phenoxy]acetic acid, sodium salt The title compound was prepared by the method of example 1 steps (iv-v) using the product from step (i)
1H NMR: DMSO-d6: δ 7.68-7.66 (2H, m), 7.56-7.54 (1H, d), 7.50-7.49 (1H, m), 7.20-7.07 (3H, m), 4.21 (2H, s), 2.58 (6H, s).
MS: ESI (−ve) 418 (M−1)

EXAMPLE 41

(2S)-2-[2-{4-[(Dimethylamino)sulfonyl]phenoxy}-4-(trifluoromethyl)phenoxy]propanoic acid, sodium salt

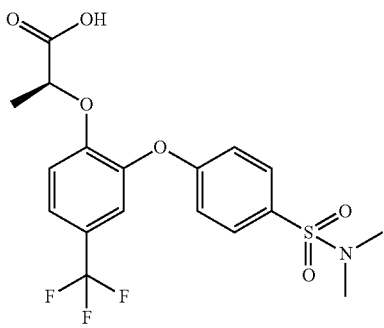 [SMILES: C[C@H](Oc1ccc(C(F)(F)F)cc1Oc1ccc(S(=O)(=O)N(C)C)cc1)C(=O)O]

The title compound was prepared by the method of example 16 using the product from example 40 step (i).
1H NMR: DMSO-d6: δ 7.68-7.64 (2H, m), 7.55-7.51 (2H, m), 7.22-7.20 (2H, m), 7.07-7.05 (1H, d), 4.35-4.30 (1H, m), 2.57 (6H, s), 1.12-1.09 (3H, d).
MS: ESI (−ve) 432 (M−1)

EXAMPLE 42

{2-[2-Chloro-4-(methylsulfonyl)phenoxy]-4-fluorophenoxy}acetic acid

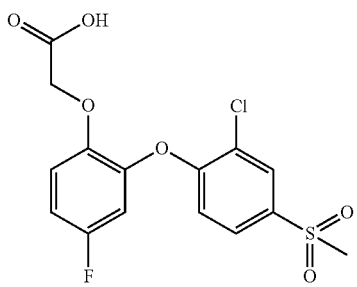 [SMILES: CS(=O)(=O)c1ccc(Oc2cc(F)ccc2OCC(=O)O)c(Cl)c1]

(i) tert-Butyl (4-fluoro-2-methoxyphenoxy)acetate

The subtitle compound was prepared by the method of example 1 step (iv) using 4-fluoro-2-methoxyphenol, yield 1.0 g.
MS: ESI (−ve) 201 (M-t-butyl)

(ii) (4-Fluoro-2-hydroxyphenoxy)acetic acid

The subtitle compound was prepared by the method of example 28 step (iii) using the product from step (i), yield 0.72 g.
MS: ESI (−ve) 185 (M−1)

(iii) {2-[2-Chloro-4-(methylsulfonyl)phenoxy]-4-fluorophenoxy}acetic acid

The title compound was prepared by the method of example 1 step (ii) using the product from step (ii) and the product from example 7 step (ii).
1H NMR: DMSO-d6: δ 8.08 (1H, s), 7.78-7.75 (1H, d), 7.25-7.22 (1H, m), 7.16-7.15 (2H, m), 6.96-6.93 (1H, d), 4.69 (2H, s), 3.24 (3H, s).
MS: ESI (−ve) 373 (M−1)

EXAMPLE 43

{2-[2-Chloro-4-(ethylsulfonyl)phenoxy]-4-fluorophenoxy}acetic acid

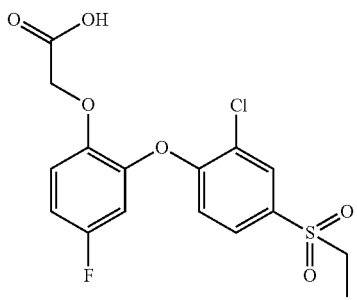 [SMILES: CCS(=O)(=O)c1ccc(Oc2cc(F)ccc2OCC(=O)O)c(Cl)c1]

The title compound was prepared by the method of example 42 using the product from example 8 step (i).

1H NMR: DMSO-d6: δ 8.00-7.99 (1H, m), 7.72-7.69 (1H, d), 7.21-7.02 (4H, m), 4.43 (2H, s), 3.40-3.30 (2H, q), 1.12-1.07 (3H, t).

MS: ESI (−ve) 387 (M−1)

EXAMPLE 44

2-{2-[2-Chloro-4-(methylsulfonyl)phenoxy]-4-fluorophenoxy}-2-methylpropanoic acid

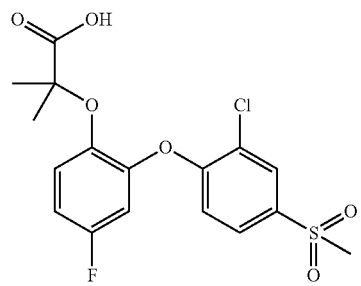 [SMILES: CC(C)(Oc1ccc(F)cc1Oc1ccc(S(C)(=O)=O)cc1Cl)C(=O)O]

(i) tert-Butyl 2-(4-fluoro-2-methoxyphenoxy)-2-methylpropanoate

Potassium carbonate (0.97 g) was added to a solution of 2-methoxy-4-fluorophenol (1.0 g) and tert-butyl-2-bromoisobutyrate (1.31 ml) in acetonitrile (20 ml) and heated under reflux for 26 h. The mixture was diluted with water and extracted with ethyl acetate, the organics were dried and evaporated under reduced pressure. The residue was purified by chromatography on silica eluting with using isohexane:diethylether 3:1, yield 0.83 g.

1H NMR: CDCl₃: δ 6.94-6.89 (1H, m), 6.64-6.59 (1H, m), 6.55-6.49 (1H, m), 3.79 (3H, s), 1.52-1.41 (15H, 2×s).

(ii) 2-(4-Fluoro-2-hydroxyphenoxy)-2-methylpropanoic acid

The subtitle compound was prepared by the method of example 28 step (iii) using the product from step (i), yield 0.7 g.

MS: ESI (−ve) 213 (M−1)

(iii) 2-{2-[2-Chloro-4-(methylsulfonyl)phenoxy]-4-fluorophenoxy}-2-methylpropanoic acid The title compound was prepared by the method of example 1 step (ii) using the product from step (ii), yield 0.065 g 1H NMR: DMSO-d6: δ 8.08-8.07 (1H, s), 7.79-7.75 (1H, d), 7.27-7.23 (1H, m), 7.12-7.09 (2H, m), 6.97-6.95 (1H, d), 3.24 (3H, s), 1.23 (6H, s).

MS: ESI (−ve) 401 (M−1)

EXAMPLE 45

(2-{[2-Chloro-4-(methylsulfonyl)phenyl]thio}-4-fluorophenoxy)acetic acid

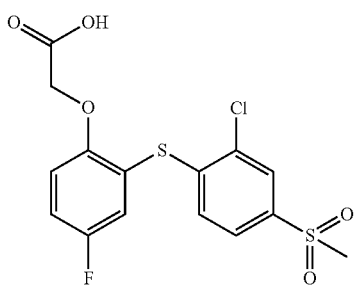 [SMILES: CS(=O)(=O)c1ccc(Sc2cc(F)ccc2OCC(=O)O)c(Cl)c1]

(i) 5-Fluoro-2-methoxybenzenesulfonyl chloride

4-Fluoroanisole (10.0 g) was carefully added to chlorosulphonic acid (45.81 g) at 0° C. The mixture was stirred at RT for 2 h, then quenched with ice-water (500 ml) and the solid filtered and dried, yield 16.50 g.

1H NMR: CDCl₃: δ 7.72-7.68 (1H, m), 7.44-7.38 (1H, m) 7.12-7.08 (1H, m), 4.05 (3H, s).

(ii) 5-Fluoro-2-methoxybenzenethiol

The subtitle compound was prepared by the method of example 1 step (i) using the product from step (i), yield 1.7 g.

MS: ESI (−ve) 157 (M−1)

(iii) 3-Chloro-4-[(5-fluoro-2-methoxyphenyl)thio]phenyl methyl sulfone

The subtitle compound was prepared by the method of example 1 step (ii) using the is product from step (ii) and the product from example 7 step (ii), yield 0.8 g.

1H NMR: CDCl₃: δ 7.91-7.90 (1H, s), 7.59-7.56 (1H, d) 7.26-7.17 (2H, m), 7.00-6.96 (1H, m), 6.82-6.79 (1H, d), 3.80 (3H, s), 3.03 (3H, s).

(iv) 2-{[2-Chloro-4-(methylsulfonyl)phenyl]thio}-4-fluorophenol

The subtitle compound was prepared by the method of example 1 step (iii) using the product from step (iii), yield 0.6 g.

MS: ESI (−ve) 331 (M−1)

(v) (2-{[2-Chloro-4-(methylsulfonyl)phenyl]thio}-4-fluorophenoxy)acetic acid

Sodium hydride (60% disp. oil, 0.024 g) was added to the product from step (iv) (0.20 g) in dry DMF (10 ml) and stirred at RT for 30 min before adding methyl-bromoacetate (0.060 ml). The solution was stirred at RT for 2 h, diluted with water and extracted with diethylether. The organics were dried and evaporated under reduced pressure to give an oil. The oil was dissolved in THF (20 ml) and water (10 ml) then sodium hydroxide (0.037 g) was added and stirred at RT overnight.

EXAMPLE 46

(2-{[2-Chloro-4-(ethylsulfonyl)phenyl]thio}-4-fluorophenoxy)acetic acid

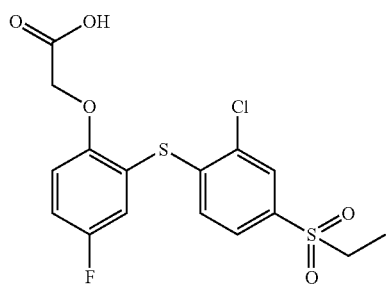 [SMILES: CCS(=O)(=O)c1ccc(Sc2cc(F)ccc2OCC(=O)O)c(Cl)c1]

The title compound was prepared by the method of example 45 using the product from example 8 step (i), yield 0.029 g.

1H NMR: DMSO-d6: δ 7.92 (1H, s), 7.64-7.61 (1H, d), 7.44-7.34 (2H, m), 7.10-7.06 (2H, m), 4.55 (2H, s), 3.41-3.28 (2H, q), 1.11-1.06 (3H, t).

MS: ESI (−ve) 403 (M−1)

EXAMPLE 47

2-(2-{[2-Chloro-4-(methylsulfonyl)phenyl]thio}-4-fluorophenoxy)-2-methylpropanoic acid

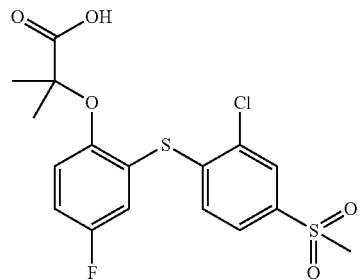

The title compound was prepared by the method of example 29 step (ii) using the product from example 45 step (iv), yield 0.05 g.

1H NMR: DMSO-d6: δ 7.98-7.97 (1H, s), 7.70-7.67 (1H, d), 7.32-7.20 (2H, m), 7.07-7.02 (2H, m), 3.24 (3H, s), 1.21 (6H, s).

MS: ESI (−ve) 417 (M−1)

EXAMPLE 48

[4-Chloro-2-(3-cyanobenzyl)phenoxy]acetic acid

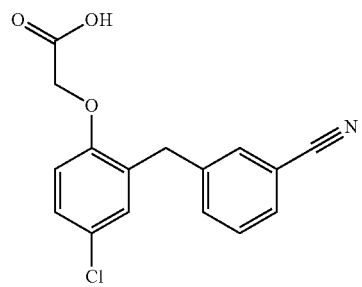 [SMILES: N#Cc1cccc(Cc2cc(Cl)ccc2OCC(=O)O)c1]

(i) 3-[2-(Benzyloxy)-5-chlorobenzyl]benzonitrile

A mixture of 2-benzyloxy-5-chlorophenylboronic acid (2.1 g), 3-cyanobenzyl bromide (1.57 g), sodium carbonate (1.7 g) and tetrakis(triphenylphosphine)palladium (0) (0.46 g) in ethylene glycol dimethyl ether (30 ml) was heated at 80° C. for 5 h. The mixture was cooled, partitioned between water/diethylether, the organics separated, dried and evaporated under reduced pressure. The residue was purified by chromatography on silica eluting with 5% ethylacetate/isohexane, yield 0.53 g.

$^1$H NMR DMSO-d6: δ 7.68-7.24 (11H, m); 7.08 (1H, d); 5.10 (2H, s); 3.97 (2H, s)

(ii) [4-Chloro-2-(3-cyanobenzyl)phenoxy]acetic acid

The title compound was prepared by the method of example 1 steps (iii-v) using the product from step (i), yield 0.175 g.

$^1$H NMR DMSO-d6: δ 7.81 (1H, s); 7.68-7.63 (2H, m); 7.47 (1H, t); 7.34 (1H, d); 7.24 (1H, dd); 6.93 (1H, d); 4.74 (2H, s); 3.99 (2H, s)

MS: APCI (−ve) 300/302 (M−1)

EXAMPLE 49

(2-{2-Chloro-4-[(ethylsulfonyl)amino]phenoxy}-4-fluorophenoxy)acetic acid

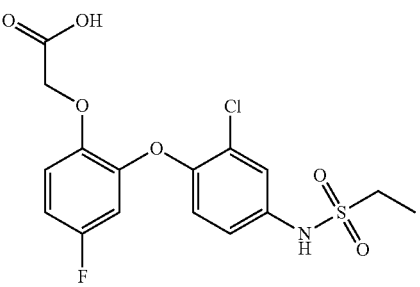 [SMILES: CCS(=O)(=O)Nc1ccc(Oc2cc(F)ccc2OCC(=O)O)c(Cl)c1]

(i) 2-Chloro-1-(5-fluoro-2-methoxyphenoxy)-4-nitrobenzene

Sodium hydride (60% disp. oil, 0.281 g) was added to a solution of 5-fluoro-2-methoxyphenol (1.0 g) in DMF (20 ml) and stirred at RT for 30 min. 2-Chloro-1-fluoro-4-nitrobenzene (1.23 g) was added and the mixture stirred at RT for 16 h then diluted with water and extracted with diethylether. The organics were dried and evaporated under reduced pressure, yield 1.95 g.
MS: ESI (−ve) 296 (M−1)

(ii) 3-Chloro-4-(5-fluoro-2-methoxyphenoxy)aniline

Iron powder (2.0 g) was added to a solution of the product from step (i) (1.95 g) in acetic acid (40 ml) and the mixture stirred at RT overnight. The mixture was filtered and the filtrate evaporated under reduced pressure. The residue was partitioned between aqueous sodium hydrogencarbonate soln and ethylacetate, the organics dried and evaporated under reduced pressure.
MS: ESI (+ve) 268 (M+1)

(iii) 2-(4-Amino-2-chlorophenoxy)-4-fluorophenol

The subtitle compound was prepared by the method of example 1 step (iii) using the product from step (ii), yield 0.75 g.
MS: ESI (−ve) 252 (M−1)

(iv) tert-Butyl [2-(4-amino-2-chlorophenoxy)-4-fluorophenoxy]acetate

The subtitle compound was prepared by the method of example 1 step (iv) using the product from step (iii), yield 0.38 g.
$^1$H NMR CDCl$_3$: δ 6.96-6.33 (6H, m); 4.62 (2H, s); 3.68 (2H, s); 1.47 (9H, s)

(v) (2-{2-Chloro-4-[(ethylsulfonyl)amino]phenoxy}-4-fluorophenoxy)acetic acid

Ethane sulphonyl chloride (0.05 ml) was added to a solution of the product from step (iv) (0.19 g) in pyridine (10 ml) and stirred at RT for 2 h. The solvent was evaporated under reduced pressure and the residue dissolved in DCM (10 ml) and trifluoroacetic acid (10 ml). After stirring at RT for 2 h the solvent was removed and the residue purified by RPHPLC, yield 0.062 g.
$^1$H NMR DMSO-d6: δ 7.36-6.74 (6H, m); 4.59 (2H, s); 3.16-3.08 (2H, q); 1.22-1.18 (3H, t)
MS: ESI (−ve) 402 (M−1)

EXAMPLE 50

(2S)-2-(4-Chloro-2-{[2-chloro-4-(ethylsulfonyl)phenyl]amino}phenoxy)propanoic acid

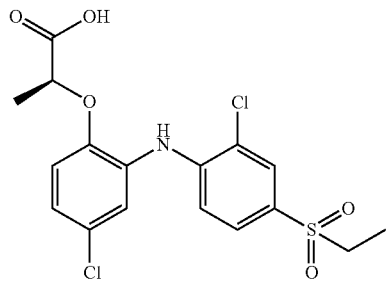 [SMILES: CCS(=O)(=O)c1ccc(Nc2cc(Cl)ccc2O[C@@H](C)C(=O)O)c(Cl)c1]

(i) 4-Chloro-2-{[2-chloro-4-(ethylsulfonyl)phenyl]amino}phenol

The subtitle compound was prepared by the method of example 1 step (ii) using the product from example 8 step (i) (1.0 g) and 5-chloro-2-benzoxazolone (0.85 g), yield 0.55 g.
MS: ESI (−ve) 345 (M−1)

(ii) (2S)-2-(4-Chloro-2-{[2-chloro-4-(ethylsulfonyl)phenyl]amino}phenoxy)propanoic acid The title compound was prepared by the method of example 16 using the product from step (i) (0.24 g), yield 0.04 g.
$^1$H NMR DMSO-d6: δ 8.84 (1H, bs); 7.80 (1H, s); 7.58 (1H, s); 7.34 (1H, s); 7.17-7.06 (3H, m); 4.60 (1H, q); 3.24 (2H, q); 1.36 (3H, d); 1.09 (3H, t)
MS: ESI (−ve) 416 (M−1)

EXAMPLE 51

2-(4-Chloro-2-{[2-chloro-4-(ethylsulfonyl)phenyl]amino}phenoxy)-2-methylpropanoic acid

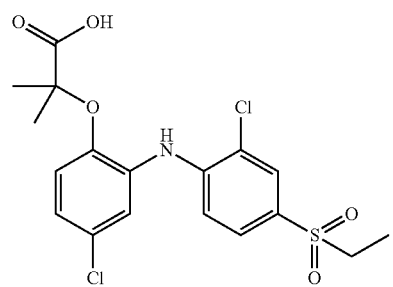 [SMILES: CCS(=O)(=O)c1ccc(Nc2cc(Cl)ccc2OC(C)(C)C(=O)O)c(Cl)c1]

The title compound was prepared by the method of example 29 step (ii) using the product from example 50 step (i), yield 0.16 g.
$^1$H NMR DMSO-d6: δ 8.15 (1H, bs); 7.83 (1H, s); 7.60 (1H, d); 7.36 (1H, s); 7.13 (1H, d); 7.01-6.94 (2H, m); 3.27 (2H, q); 1.38 (6H, s); 1.08 (3H, t)
MS: ESI (−ve) 430 (M−1)

EXAMPLE 52

(2S)-2-(4-Chloro-2-{[2-chloro-4-(methylsulfonyl)phenyl]amino}phenoxy)propanoic acid

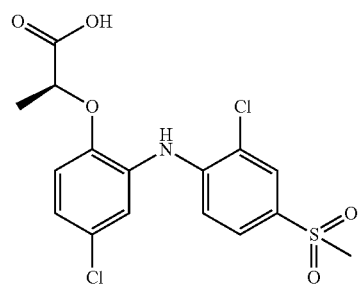 [SMILES: C[C@H](Oc1ccc(Cl)cc1Nc1ccc(S(C)(=O)=O)cc1Cl)C(=O)O]

The title compound was prepared by the method of example 50 using the product from example 7 step (ii), yield 0.075 g.

¹H NMR DMSO-d6: δ 7.94 (1H, s); 7.88 (1H, s); 7.64 (1H, d); 7.37-7.32 (1H, m); 7.20-7.06 (3H, m); 4.89 (1H, q); 3.18 (3H, s); 1.38 (3H, d)

MS: ESI (−ve) 402 (M−1)

EXAMPLE 53

2-(4-Chloro-2-{[2-chloro-4-(methylsulfonyl)phenyl]amino}phenoxy)-2-methylpropanoic acid

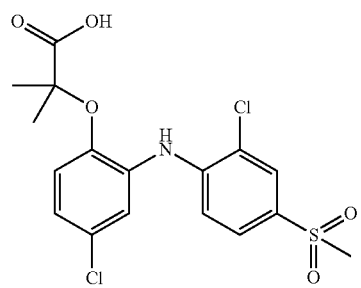 [SMILES: CC(C)(Oc1ccc(Cl)cc1Nc1ccc(S(C)(=O)=O)cc1Cl)C(=O)O]

The title compound was prepared by the method of example 50 step (i) and example 29 step (ii), yield 0.05 g.

¹H NMR DMSO-d6: δ 7.86 (1H, s); 7.64 (1H, d); 7.28-7.22 (1H, m); 7.10-7.06 (2H, m); 7.02 (1H, d); 3.17 (3H, s); 1.39 (6H, s)

MS: ESI (−ve) 416 (M−1)

EXAMPLE 54

[4-Chloro-2-(pyrimidin-5-yloxy)phenoxy]acetic acid

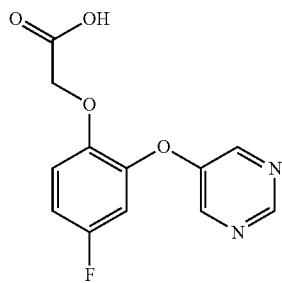 [SMILES: O=C(O)COc1ccc(F)cc1Oc1cncnc1]

A mixture of the product from example 5 step (ii) (0.2 g), 5-bromopyrimidine (0.308 g), tetramethylheptane-3,5-dione (0.046 g), cesium carbonate (0.65 g) and cuprous chloride (0.045 g) in NMP (2 ml) was heated at 130° C. overnight then at 150° C. The mixture was filtered, the filtrate washed with diethylether, acidified to pH 4 with 2M hydrochloric acid and extracted with ethylacetate. The ethylacetate layer was washed with water, dried and evaporated under reduced pressure. The residue was purified by chromatography on silica eluting with ethylacetate/acetic acid. Yield 0.007 g ¹H NMR DMSO-d6: δ 8.92 (1H, s); 8.52 (2H, s); 7.42 (1H, s); 7.33 (1H, dd); 7.13 (1H, d); 4.74 (2H, s)

MS: ESI (−ve) 279 (M−1)

EXAMPLE 55

[4-Chloro-2-(quinolin-3-yloxy)phenoxy]acetic acid

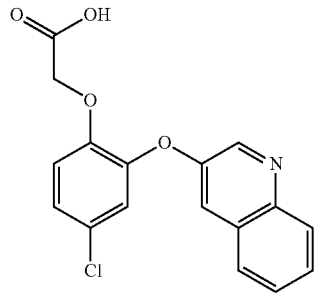 [SMILES: O=C(O)COc1ccc(Cl)cc1Oc1cnc2ccccc2c1]

The title compound was prepared by the method of example 54, yield 0.035 g.

¹H NMR DMSO-d6: δ 8.00 (1H, d); 7.84 (1H, d); 7.67-7.63 (2H, m); 7.54 (1H, t); 7.38 (1H, d); 7.32 (1H, dd); 7.17 (1H, d); 4.74 (2H, s)

MS: ESI (−ve) 328 (M−1)

EXAMPLE 56

(2-{[2-Chloro-4-(methylsulfonyl)phenyl]amino}-4-fluorophenoxy)acetic acid

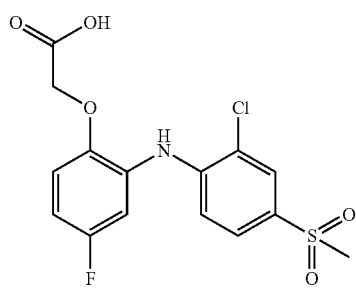 [SMILES: CS(=O)(=O)c1ccc(Nc2cc(F)ccc2OCC(=O)O)c(Cl)c1]

(i) 2-Chloro-N-(5-fluoro-2-methoxyphenyl)-4-(methylsulfonyl)aniline

A mixture of 2-bromo-4-fluoroanisole (6.0 g), 2-chloro-4-methylsulphonylaniline (9.0 g), cesium carbonate (14.7 g), palladium acetate (0.33 g) and 2-(dicyclohexylphosphino)-2',4',6'-tri-1-propyl-1,1'-biphenyl (0.54 g) in dioxane (60 ml) was heated at 100° C. for 20 h. The mixture was cooled, and partitioned between ethylacetate/water. The organics were separated, washed with brine, dried and evaporated under reduced pressure. The residue was purified by chromatography on silica eluting with 25% ethylacetate/isohexane. Yield 3.2 g MS: ESI (+ve) 330 (M+1)

(ii) 2-{[2-Chloro-4-(methylsulfonyl)phenyl]amino}-4-fluorophenol

The subtitle compound was prepared by the method of example 1 step (iii) using the product from step (i), yield 2.2 g.

MS: ESI (+ve) 316 (M+1)

(iii) (2-{[2-Chloro-4-(methylsulfonyl)phenyl]amino}-4-fluorophenoxy)acetic acid

Sodium tert-butoxide (0.073 g) was added to a solution of the product from step (ii) (0.2 g) in THF (10 ml) and stirred at RT for 5 min. Ethyl bromoacetate (0.078 ml) was added, the mixture stirred for 1 h before adding 2M sodium hydroxide solution (2 ml). After 3 h, 2M hydrochloric acid was added and the mixture extracted with ethyl acetate. The organics is were washed with brine, dried and evaporated under reduced pressure. The residue was purified by RPHPLC, yield 0.11 g.

$^1$H NMR DMSO-d6: δ 13.14 (s, 1H), 7.97 (s, 1H), 7.89 (s, 1H), 7.64 (d, 1H), 7.20 (d, 1H), 7.12 (m, 2H), 6.98 (m, 1H), 4.75 (s, 2H), 3.18 (s, 3H)

MS: ESI (−ve) 372 (M−1)

EXAMPLE 57

(2S)-2-(2-{[2-Chloro-4-(methylsulfonyl)phenyl]amino}-4-fluorophenoxy)propanoic acid

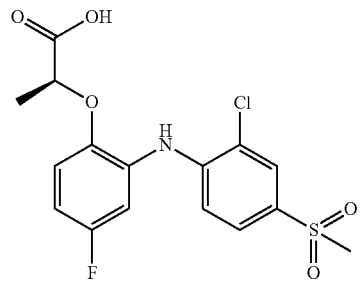 [SMILES: C[C@H](Oc1ccc(F)cc1Nc1ccc(S(C)(=O)=O)cc1Cl)C(=O)O]

Diisopropyl azodicarboxylate (0.14 ml) was added to a stirred solution of the product from example 56 step (ii) (0.2 g), triphenylphosphine (0.18 g), R-methyl lactate (0.1 g) in THF (10 ml). After 20 h, aqueous 1M sodium hydroxide solution (2 ml) was added and stirred for 4 h. The mixture was diluted with water (30 ml) then partitioned between ethyl acetate/2M hydrochloric acid. The organics were separated, washed with brine, dried and evaporated under reduced pressure. The residue was purified by RPHPLC, yield 0.094 g.

$^1$H NMR DMSO-d6: δ 13.23 (s, 1H), 7.99 (s, 1H), 7.90 (s, 1H), 7.66 (d, 1H), 7.22 (m, 2H), 7.12 (m, 1H), 6.96 (m, 1H), 4.86 (q, 1H), 3.18 (s, 3H), 1.43 (d, 3H)

MS: ESI (−ve) 386 (M−1)

EXAMPLE 58

{4-Chloro-2-[[2-chloro-4-(methylsulfonyl)phenyl](methyl)amino]phenoxy}acetic acid

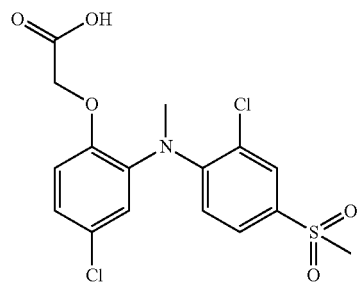 [SMILES: CN(c1ccc(S(C)(=O)=O)cc1Cl)c1cc(Cl)ccc1OCC(=O)O]

Sodium hydride (60% disp. oil, 0.11 g) was added to a solution of the product from example 31 (0.5 g) in DMF (5 ml) and stirred at RT for 10 min. Methyl iodide (1 ml) was added, stirred for 5 h then methanol (1 ml) added followed by 1M sodium hydroxide solution (3 ml). After stirring for a further 20 h the mixture was acidified with 2M hydrochloric acid and extracted with ethyl acetate. The organics were washed with brine, dried and evaporated under reduced pressure. The residue was purified by RPHPLC, yield 0.21 g.

$^1$H NMR DMSO-d6: δ 13.01 (s, 1H), 7.82 (d, 1H), 7.81 (s, 1H), 7.43 (d, 1H), 7.15 (d, 1H), 7.00 (d, 1H), 6.84 (s, 1H), 4.69 (s, 2H), 3.27 (s, 3H), 3.23 (s, 3H)

MS: ESI (−ve) 402 (M−1)

EXAMPLE 59

{4-Chloro-2-[[2-chloro-4-(methylsulfonyl)phenyl](ethyl)amino]phenoxy}acetic acid

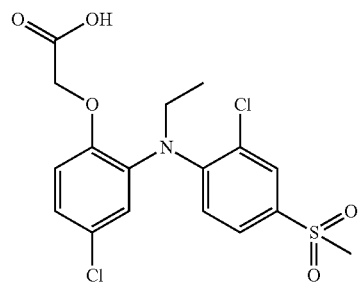 [SMILES: CCN(c1ccc(S(C)(=O)=O)cc1Cl)c1cc(Cl)ccc1OCC(=O)O]

The title compound was prepared by the method of example 58 using iodoethane, yield 0.017 g.

$^1$H NMR DMSO-d6: δ 7.79 (s, 1H), 7.78 (d, 1H), 7.44 (d, 1H), 7.13 (d, 1H), 6.99 (d, 1H), 6.82 (s, 1H), 4.63 (s, 2H), 3.80 (q, 2H), 3.23 (s, 3H), 1.13 (t, 3H)

MS: ESI (−ve) 416 (M−1)

EXAMPLE 60

(2-{[2-Chloro-4-(ethylsulfonyl)phenyl]amino}-4-fluorophenoxy)acetic acid

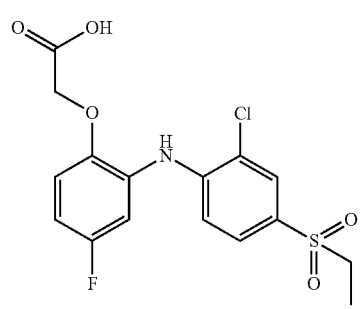

(i) 5-Fluoro-1,3-benzoxazol-2(3H)-one

A solution of 2-amino-4-fluorophenol (4.0 g), carbonyldiimidazole (1.7 g) in DCM (100 ml) and acetonitrile (30 ml) was stirred at RT for 5 h. The solvent was removed under reduced pressure and the residue purified by chromatography on silica eluting with 30% ethylacetate/isohexane, yield 4.0 g.

MS: ESI (+ve) 154 (M+1)

(ii) 2-{[2-Chloro-4-(ethylsulfonyl)phenyl]amino}-4-fluorophenol

A mixture of the product from step (i) (1.38 g), the product from example 8 step (i) (2.0 g) and potassium carbonate (3.7 g) in NMP (20 ml) was heated in a CEM microwave (100° C./50 watts) for 15 min. Methanol (30 ml) followed by 1M sodium hydroxide solution were added and the reaction stirred at RT for 3 h. The mixture was acidified with 2M hydrochloric acid, extracted with ethyl acetate, the organics washed with water, brine, dried and evaporated under reduced pressure. The residue was purified by chromatography on silica eluting with 25% ethylacetate/isohexane, yield 2.0 g.

MS: ESI (+ve) 330 (M+1)

(iii) (2-{[2-Chloro-4-(ethylsulfonyl)phenyl]amino}-4-fluorophenoxy)acetic acid The title compound was prepared by the method of example 56 step (iii) using the product from step (ii), yield 0.35 g.

$^1$H NMR DMSO-d6: δ 13.14 (s, 1H), 7.99 (s, 1H), 7.82 (s, 1H), 7.59 (d, 1H), 7.22 (d, 1H), 7.12 (s, 1H), 7.11 (d, 1H), 6.99 (m, 1H), 4.74 (s, 2H), 3.25 (q, 2H), 1.10 (t, 3H)

MS: ESI (−ve) 386 (M−1)

EXAMPLE 61

{2-[2-Chloro-4-(methylsulfonyl)phenoxy]phenoxy}acetic acid

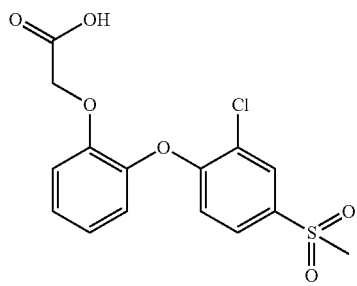 [SMILES: CS(=O)(=O)c1ccc(Oc2ccccc2OCC(=O)O)c(Cl)c1]

Sodium hydride (60% disp. oil, 0.24 g) was added to a solution of (2-hydroxyphenoxy)acetic acid (0.5 g) in DMF (20 ml) and stirred at 40° C. for 30 min. The product from example 7 step (ii) (0.62 g) was added, then the mixture heated at 75° C. for 30 h. 2M Sodium hydroxide solution was added and extracted with ethylacetate. The aqueous layer was acidified with 2M hydrochloric acid and extracted with ethyl acetate. The organics were dried, evaporated under reduced pressure and the residue purified by RPHPLC, yield 0.21 g.

$^1$H NMR DMSO-d6: δ 8.05-6.93 (7H, m); 4.47 (2H, s); 3.23 (3H, s)

MS: APCI (−ve) 355 (M−1)

EXAMPLE 62

{4-Chloro-2-[4-(methylsulfonyl)-3-(trifluoromethyl)phenoxy]phenoxy}acetic acid

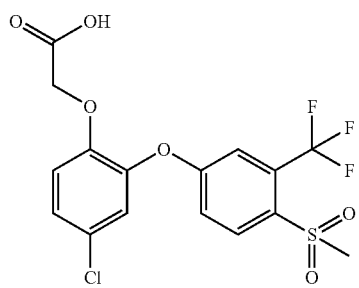 [SMILES: CS(=O)(=O)c1ccc(Oc2cc(Cl)ccc2OCC(=O)O)cc1C(F)(F)F]

(i) 4-Bromo-2-(trifluoromethyl)phenyl methyl sulfide

A mixture of sodium thiomethoxide (0.317 g) and 5-bromo-2-fluorobenzotrifluoride (1.0 g) in DMF (4 ml) was heated at 50° C. for 1 h then poured into water and extracted with isohexane. The organics were washed with brine, dried and evaporated under reduced pressure. Yield 0.762 g $^1$H NMR DMSO-d6: δ 7.74 (1H, d); 7.59 (1H, dd); 7.22 (1H, d); 2.51 (3H, s)

(ii) 4-Bromo-2-(trifluoromethyl)phenyl methyl sulfone

The subtitle compound was prepared by the method of example 2 step (ii) using the product from step (i), yield 0.8 g.

(iii) Methyl {4-chloro-2-[4-(methylsulfonyl)-3-(trifluoromethyl)phenoxy]phenoxy}acetate A mixture of sodium tert-butoxide (0.96 g), the product from example 5 step (ii) (0.4 g) in DMSO (10 ml) was stirred at RT for 1 h, then the product from step (ii) (0.66 g) added. The mixture was heated at 120° C. for 6 h, cooled and partitioned between ethyl acetate/2M hydrochloric acid. The organics were separated, washed with water, dried and evaporated under reduced pressure. The residue was esterified using trimethyldiazomethane in DCM/methanol, yield 0.205 g.

$^1$H NMR CDCl$_3$: δ 8.22 (1H, d); 7.47 (1H, d); 7.27-7.13 (3H, m); 6.86 (1H, d); 4.61 (2H, s); 3.74 (3H, s); 3.17 (3H, s);

(iv) {4-Chloro-2-[4-(methylsulfonyl)-3-(trifluoromethyl)phenoxy]phenoxy}acetic acid 1M Sodium hydroxide solution (0.5 m) was added to a solution of the product from step (iii) (0.197 g) in methanol (1 ml) and tetrahydrofuran (3 ml) and stirred at RT for 16 h. The solvent was evaporated under reduced pressure and the residue partitioned between DCM/2M hydrochloric acid. The organics were dried, evaporated under reduced pressure and the residue recrystallised from DCM-isohexane, yield 0.108 g.

$^1$H NMR DMSO-d6: δ 13.10 (1H, s); 8.16 (1H, d); 7.51 (1H, d); 7.46 (1H, d); 7.38 (1H, dd); 7.33 (1H, dd); 7.18 (1H, d); 4.75 (2H, s); 3.24 (3H, s)

MS: APCI (−ve) 423 (M−1)

EXAMPLE 63

[4-Chloro-2-(quinolin-8-ylthio)phenoxy]acetic acid

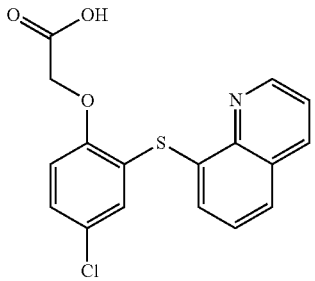 [SMILES: O=C(O)COc1ccc(Cl)cc1Sc1cccc2cccnc12]

(i) tert-Butyl (4-chloro-2-iodophenoxy)acetate

The subtitle compound was prepared by the method of example 1 step (iv) using 4-chloro-2-iodo-phenol (4.75 g), yield 6.88 g.

$^1$H NMR CDCl$_3$: δ 7.77 (1H, d); 7.24 (1H, dd); 6.61 (1H, d); 4.55 (2H, s); 1.48 (9H, s)

(ii) [4-Chloro-2-(quinolin-8-ylthio)phenoxy]acetic acid

A mixture of the product from step (i) (0.262 g), 8-quinolinethiol hydrochloride (0.141 g), copper (I) iodide (7 mg), potassium carbonate (0.295 g) and ethylene glycol (0.08 ml) in iso-propanol (3 ml) was heated at 80° C. for 48 h. The mixture was partitioned between DCM/2M hydrochloric acid, the organics dried, evaporated under reduced pressure and the residue purified by chromatography on silica eluting with DCM:methanol:acetic acid (90:9:1). The residue was triturated with diethylether/methanol, filtered and dried, yield 0.101 g.

$^1$H NMR DMSO-d6: δ 13.00 (1H, bs); 8.95 (1H, d); 8.42 (1H, d); 7.81 (1H, d); 7.63 (1H, dd); 7.57-7.37 (3H, m); 7.08 (2H, d); 4.79 (2H, s)

MS: APCI (−ve) 344/6 (M−1)

EXAMPLE 64

(2S)-2-[4-Chloro-2-(4-nitrophenoxy)phenoxy]-propanoic acid

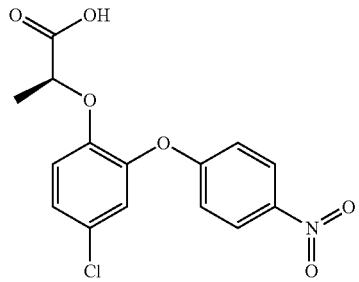 [SMILES: C[C@H](Oc1ccc(Cl)cc1Oc1ccc([N+](=O)[O-])cc1)C(=O)O]

(i) Methyl (2S)-2-(4-chloro-2-formylphenoxy)propanoate

The subtitle compound was prepared by the method of example 1 step (ii) using 5-chloro-2-hydroxybenbaldehyde and methyl (2R)-2-(4-toluenesulphonyl)lactate $^1$H NMR CDCl$_3$: δ 10.50 (1H, s); 7.81 (1H, d); 7.44 (1H, dd); 6.79 (1H, d); 4.87 (1H, q); 3.77 (3H, s); 1.70 (3H, d)

(ii) (2S)-2-(4-Chloro-2-hydroxyphenoxy)propanoic acid

The subtitle compound was prepared by the method of example 1 step (ii) and example 26 step (iv) using the product from step (i).

MS: APCI (−ve) 215/7 (M−1)

(iii) (2S)-2-[4-Chloro-2-(4-nitrophenoxy)phenoxy]-propanoic acid

To a solution of (2S)-2-(4-chloro-2-hydroxyphenoxy)-propanoic acid (0.216 g) and 1-fluoro-4-nitro-benzene (0.127 g) in NMP (3 ml) was added potassium carbonate (0.276 g) and the reaction heated at 90° C. for 2 h. After cooling to RT, water and diethylether were added. The aqueous layer was separated and extracted again with diethylether. The aqueous layer was isolated, acidified to pH 2 and extracted with diethylether. This later extract was dried and evaporated under reduced pressure. The residue was purified by chromatography on silica eluting with 30-50% ethyllactate/isohexane+1% AcOH, yield 0.2 g $^1$H NMR DMSO-d6: δ 8.22 (2H, d), 7.40 (1H, d), 7.34 (1H, dd), 7.09 (3H, m), 4.85 (1H, q), 1.26 (3H, d).

MS: APCI (−ve) 336

EXAMPLE 65

(2S)-2-(2-{[2-Chloro-4-(ethylsulfonyl)phenyl]amino}-4-fluorophenoxy)propanoic acid

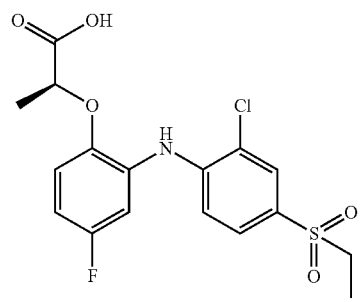 [SMILES: CCS(=O)(=O)c1ccc(Nc2cc(F)ccc2O[C@@H](C)C(=O)O)c(Cl)c1]

The title compound was prepared by the method of example 57 using the product from example 60 step (ii).

$^1$H NMR DMSO-d6: δ 13.22 (s, 1H), 8.04 (s, 1H), 7.83 (s, 1H), 7.61 (d, 1H), 7.24 (d, 1H), 7.18 (d, 1H), 7.12 (m, 1H), 6.97 (m, 1H), 4.85 (q, 1H), 3.26 (q, 2H), 1.42 (d, 3H), 1.10 (t, 3H)

MS: APCI (−ve) 400

EXAMPLE 66

2-(2-{[2-Chloro-4-(ethylsulfonyl)phenyl]amino}-4-fluorophenoxy)-2-methylpropanoic acid, sodium salt

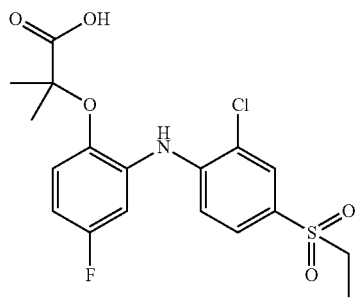 [SMILES: CCS(=O)(=O)c1ccc(Nc2cc(F)ccc2OC(C)(C)C(=O)O)c(Cl)c1]

The title compound was prepared by the method of example 29 step (ii) using the product from example 60 step (ii).

$^1$H NMR DMSO-d6: δ 10.67 (s, 1H), 7.77 (s, 1H), 7.56 (d, 1H), 7.22 (d, 1H), 7.04 (m, 2H), 6.75 (m, 1H), 3.24 (q, 2H), 1.38 (s, 6H), 1.10 (t, 3H)

MS: APCI (−ve) 414

EXAMPLE 67

[2-{[2-Chloro-4-(methylsulfonyl)phenyl]amino}-4-(trifluoromethyl)phenoxy]acetic acid

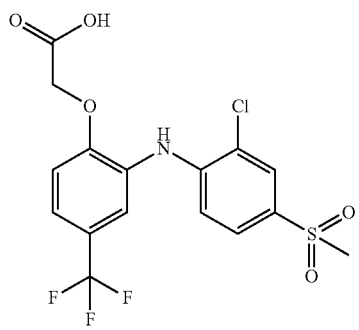 [SMILES: CS(=O)(=O)c1ccc(Nc2cc(C(F)(F)F)ccc2OCC(=O)O)c(Cl)c1]

(i) 2-{[2-Chloro-4-(methylsulfonyl)phenyl]amino}-4-(trifluoromethyl)phenol

The subtitle compound was prepared by the method of example 60 step (ii) using 5-(trifluoromethyl)-1,3-benzoxazol-2(3H)-one and the product from example 7 step (ii).

MS: ESI (+ve) 366 (M+1)

(ii) [2-{[2-Chloro-4-(methylsulfonyl)phenyl]amino}-4-(trifluoromethyl)phenoxy]acetic acid The title compound was prepared by the method of example 56 step (iii) using the product from step (i).

$^1$H NMR DMSO-d6: δ 8.50 (s, 1H), 7.86 (s, 1H), 7.59 (m, 2H), 7.49 (d, 1H), 7.19 (d, 1H), 7.02 (d, 1H), 4.60 (s, 2H), 3.17 (s, 3H)

MS: APCI (−ve) 422 (M−1)

EXAMPLE 68

[2-{[2-Chloro-4-(ethylsulfonyl)phenyl]amino}-4-(trifluoromethyl)phenoxy]acetic acid

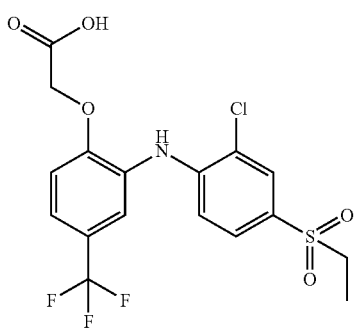

(i) 2-{[2-Chloro-4-(ethylsulfonyl)phenyl]amino}-4-(trifluoromethyl)phenol

The subtitle compound was prepared by the method of example 60 step (ii) using 5-(trifluoromethyl)-1,3-benzoxazol-2(3H)-one and the product from example 8 step (i).

MS: ESI (+ve) 380 (M+1)

(ii) [2-{[2-Chloro-4-(ethylsulfonyl)phenyl]amino}-4-(trifluoromethyl)phenoxy]acetic acid The title compound was prepared by the method of example 56 step (iii) using the product from step (i).

$^1$H NMR DMSO-d6: δ 13.18 (s, 1H), 8.09 (s, 1H), 7.81 (s, 1H), 7.63 (s, 1H), 7.55 (m, 2H), 7.23 (d, 1H), 6.87 (d, 1H), 4.85 (s, 2H), 3.24 (q, 2H), 1.10 (t, 3H)

MS: APCI (−ve) 436 (M−1)

Pharmacological Data

Ligand Binding Assay

[$^3$H]PGD$_2$ was purchased from Perkin Elmer Life Sciences with a specific activity of 100-210 Ci/mmol All other chemicals were of analytical grade.

HEK cells expressing rhCRTh2/Ga16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 μg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C.

The final pellet was re-suspended in 4 ml of membrane homogenisation buffer per cell factory used and the protein content determined Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM.

Specifically, example 4 has a pIC$_{50}$=8.0, example 5 has a pIC$_{50}$=8.0 and example 43 has a pIC$_{50}$=9.0.

The invention claimed is:

1. A compound selected from:
[4-Chloro-2-[[4-(ethylsulfonyl)phenyl]thio]phenoxy]-acetic acid,
[4-Chloro-2-[[4-(ethylsulfonyl)-2-methylphenyl]thio]phenoxy]-acetic acid,
[4-Chloro-2-[4-(ethylsulfonyl)phenoxy]phenoxy]-acetic acid,
[4-Chloro-2-[[4-(methylsulfonyl)phenyl]amino]phenoxy]-acetic acid,
(4-Chloro-2-{[2-chloro-4-(methylsulfonyl)phenyl]thio}phenoxy)acetic acid,
(4-Chloro-2-{[2-chloro-4-(ethylsulfonyl)phenyl]thio}phenoxy)acetic acid,
(4-Chloro-2-{[4-(methylsulfonyl)phenyl]thio}phenoxy)acetic acid,
{4-Chloro-2-[(5-chloropyridin-2-yl)thio]phenoxy}acetic acid,
{4-Chloro-2-[(2-chloro-4-cyanophenyl)thio]phenoxy}acetic acid,
(4-Chloro-2-{[2-(methylsulfonyl)phenyl]thio}phenoxy)acetic acid,
(4-Chloro-2-{4-(methylsulfonyl)phenyl]sulfinyl}phenoxy)acetic acid,
(4-Chloro-2-{[4-(methylsulfonyl)phenyl]sulfonyl}phenoxy)acetic acid,
[4-Chloro-2-({4-[(methylamino)carbonyl]phenyl}thio)phenoxy]acetic acid,
(2S)-2-(4-Chloro-2-{[4-(methylsulfonyl)phenyl]thio}phenoxy)propanoic acid,
(2R)-2-(4-Chloro-2-{[4-(methylsulfonyl)phenyl]thio}phenoxy)propanoic acid,
(2S)-2-(4-Chloro-2-{[2-chloro-4-(methylsulfonyl)phenyl]thio}phenoxy)propanoic acid,
(2S)-2-(4-Chloro-2-{[2-chloro-4-(ethylsulfonyl)phenyl]thio}phenoxy)propanoic acid,
2-(4-Chloro-2-{[2-chloro-4-(methylsulfonyl)phenyl]thio}phenoxy)-2-methylpropanoic acid,
{4-Chloro-2-[4-(methylsulfonyl)phenoxy]phenoxy}acetic acid,
{4-Chloro-2-[2-chloro-4-(methylsulfonyl)phenoxy]phenoxy}acetic acid,
{4-Chloro-2-[2-chloro-4-(ethylsulfonyl)phenoxy]phenoxy}acetic acid,
(2S)-2-{4-Chloro-2-[4-(methylsulfonyl)phenoxy]phenoxy}propanoic acid,
(2S)-2-{4-Chloro-2-[2-chloro-4-(methylsulfonyl)phenoxy]phenoxy}propanoic acid,
(2S)-2-{4-Chloro-2-[2-chloro-4-(ethylsulfonyl)phenoxy]phenoxy}propanoic acid,
{4,5-Dichloro-2-[2-chloro-4-(methylsulfonyl)phenoxy]phenoxy}acetic acid,
{2-[2-Chloro-4-(methylsulfonyl)phenoxy]-4,5-difluorophenoxy}acetic acid,
2-{4-Chloro-2-[2-chloro-4-(methylsulfonyl)phenoxy]phenoxy}-2-methylpropanoic acid,
(4-Chloro-2-{[2-chloro-4-(ethylsulfonyl)phenyl]amino}phenoxy)acetic acid,
(4-Chloro-2-{[2-chloro-4-(methylsulfonyl)phenyl]amino}phenoxy)acetic acid,
[2-{[2-Chloro-4-(methylsulfonyl)phenyl]thio}-4-(trifluoromethyl)phenoxy]acetic acid,
(2S)-2-[2-{[2-Chloro-4-(methylsulfonyl)phenyl]thio}-4-(trifluoromethyl)phenoxy]propanoic acid,
[2-{[2-Chloro-4-(ethylsulfonyl)phenyl]thio}-4-(trifluoromethyl)phenoxy]acetic acid,
(2S)-2-[2-{[2-Chloro-4-(ethylsulfonyl)phenyl]thio}-4-(trifluoromethyl)phenoxy]propanoic acid,
[2-({4-[(Dimethylamino)sulfonyl]phenyl}thio)-4-(trifluoromethyl)phenoxy]acetic acid,
[2-[2-Chloro-4-(methylsulfonyl)phenoxy]-4-(trifluoromethyl)phenoxy]acetic acid,
[2-[2-Chloro-4-(ethylsulfonyl)phenoxy]-4-(trifluoromethyl)phenoxy]acetic acid,
2-[2-[2-Chloro-4-(methylsulfonyl)phenoxy]-4-(trifluoromethyl)phenoxy]butanoic acid,
[2-{4-[(Dimethylamino)sulfonyl]phenoxy}-4-(trifluoromethyl)phenoxy]acetic acid,
(2S)-2-[2-{4-[(Dimethylamino)sulfonyl]phenoxy}-4-(trifluoromethyl)phenoxy]propanoic acid,
{2-[2-Chloro-4-(methylsulfonyl)phenoxy]-4-fluorophenoxy}acetic acid,
{2-[2-Chloro-4-(ethylsulfonyl)phenoxy]-4-fluorophenoxy}acetic acid,
2-{2-[2-Chloro-4-(methylsulfonyl)phenoxy]-4-fluorophenoxy}-2-methylpropanoic acid,
(2-{[2-chloro-4-(methylsulfonyl)phenyl]thio}-4-fluorophenoxy)acetic acid,
(2-{[2-Chloro-4-(ethylsulfonyl)phenyl]thio}-4-fluorophenoxy)acetic acid,
2-(2-{[2-Chloro-4-(methylsulfonyl)phenyl]thio}-4-fluorophenoxy)-2-methylpropanoic acid,
(2-{2-Chloro-4-[(ethylsulfonyl)amino]phenoxy}-4-fluorophenoxy)acetic acid,
(2S)-2-(4-Chloro-2-{[2-chloro-4-(ethylsulfonyl)phenyl]amino}phenoxy)propanoic acid,
2-(4-Chloro-2-{[2-chloro-4-(ethylsulfonyl)phenyl]amino}phenoxy)-2-methylpropanoic acid,
(2S)-2-(4-Chloro-2-{[2-chloro-4-(methylsulfonyl)phenyl]amino}phenoxy)propanoic acid, 2-(4-Chloro-2-{[2-chloro-4-(methylsulfonyl)phenyl]
amino}phenoxy)-2-methylpropanoic acid,
[4-Chloro-2-(pyrimidin-5-yloxy)phenoxy]acetic acid,
[4-Chloro-2-(quinolin-3-yloxy)phenoxy]acetic acid,
(2-{[2-Chloro-4-(methylsulfonyl)phenyl]amino}-4-fluorophenoxy)acetic acid,
(2S)-2-(2-{[2-Chloro-4-(methylsulfonyl)phenyl]amino}-4-fluorophenoxy)propanoic acid,
{4-Chloro-2-[[2-chloro-4-(methylsulfonyl)phenyl](methyl)amino]phenoxy}acetic acid,
{4-Chloro-2-[[2-chloro-4-(methylsulfonyl)phenyl](ethyl)amino]phenoxy}acetic acid,
(2-{[2-Chloro-4-(ethylsulfonyl)phenyl]amino}-4-fluorophenoxy)acetic acid,
{2-[2-Chloro-4-(methylsulfonyl)phenoxy]phenoxy}acetic acid,
{4-Chloro-2-[4-(methylsulfonyl)-3-(trifluoromethyl)phenoxy]phenoxy}acetic acid,
[4-Chloro-2-(quinolin-8-ylthio)phenoxy]acetic acid,
(2S)-2-[4-Chloro-2-(4-nitrophenoxy)phenoxy]-propanoic acid,
(2S)-2-(2-{[2-Chloro-4-(ethylsulfonyl)phenyl]amino}-4-fluorophenoxy)propanoic acid,
2-(2-{[2-Chloro-4-(ethylsulfonyl)phenyl]amino}-4-fluorophenoxy)-2-methylpropanoic acid,
[2-{[2-Chloro-4-(methylsulfonyl)phenyl]amino}-4-(trifluoromethyl)phenoxy]acetic acid,
[2-{[2-Chloro-4-(ethylsulfonyl)phenyl]amino}-4-(trifluoromethyl)phenoxy]acetic acid,
[2[4-(Ethylsulfonyl)benzyl]-4-(trifluoromethyl)phenoxy]acetic acid, and
[4-Chloro-2-(3-cyanobenzyl)phenoxy]acetic acid,
or a pharmaceutically acceptable salt thereof.

2. A pharmaceutical composition comprising a compound according to claim 1 or a pharmaceutically acceptable salt thereof in combination with a pharmaceutically acceptable carrier or diluent.

3. A compound which is (2S)-2-{4-Chloro-2-[2-chloro-4-(ethylsulfonyl)phenoxy]phenoxy}propanoic acid, or a pharmaceutically acceptable salt thereof.

4. A pharmaceutical composition comprising a compound according to claim 3 or a pharmaceutically acceptable salt thereof in combination with a pharmaceutically acceptable carrier or diluent.

* * * * *

UNITED STATES PATENT AND TRADEMARK OFFICE
CERTIFICATE OF CORRECTION

Page 1 of 2

PATENT NO. : 8,394,986 B2
APPLICATION NO. : 13/190881
DATED : March 12, 2013
INVENTOR(S) : Roger Victor Bonnert et al.

It is certified that error appears in the above-identified patent and that said Letters Patent is hereby corrected as shown below:

Delete title page and substitute the attached title page therefor.

In the Claims:

Column 66, line 22, please insert --Claim 5. A compound (2S)-2-{4-Chloro-2-[2-chloro-4-(ethylsulfonyl)phenoxy]phenoxy}propanoic acid.--

Column 66, after line 22, please insert --Claim 6. A pharmaceutically acceptable salt of the compound of claim 5.--

Signed and Sealed this
Twenty-eighth Day of May, 2013

Teresa Stanek Rea
*Acting Director of the United States Patent and Trademark Office*

(12) United States Patent
Bonnert et al.

(10) Patent No.: US 8,394,986 B2
(45) Date of Patent: Mar. 12, 2013

(54) PHENOXIACETIC ACID DERIVATIVES

(75) Inventors: Roger Victor Bonnert, Loughborough (GB); Anil Patel, Loughborough (GB); Stephen Thom, Loughborough (GB)

(73) Assignee: AstraZeneca AB, Cheshire (GB)

(*) Notice: Subject to any disclaimer, the term of this patent is extended or adjusted under 35 U.S.C. 154(b) by 0 days.

(21) Appl. No.: 13/190,881

(22) Filed: Jul. 26, 2011

(65) Prior Publication Data
US 2011/0281898 A1 Nov. 17, 2011

Related U.S. Application Data

(63) Continuation of application No. 10/569,065, filed as application No. PCT/GB2004/003551 on Aug. 18, 2004, now Pat. No. 8,003,703.

(30) Foreign Application Priority Data

Aug. 21, 2003 (SE) .................................. 0302281
Jun. 4, 2004 (GB) .................................. 0412448.3

(51) Int. Cl.
*C07C 63/04* (2006.01)

(52) U.S. Cl. ................................................ 562/493

(58) Field of Classification Search ................ 562/493
See application file for complete search history.

(56) References Cited

U.S. PATENT DOCUMENTS

| | | | |
|---|---|---|---|
| 3,278,524 | A | 10/1966 | Johnson et al. |
| 3,920,846 | A | 11/1975 | Hanauye et al. |
| 3,954,852 | A | 5/1976 | Shen et al. |
| 3,985,779 | A | 10/1976 | Tanaka et al. |
| 4,234,742 | A | 11/1980 | Cognacq et al. |
| 4,248,618 | A | 2/1981 | Serban et al. |
| 4,670,566 | A | 6/1987 | Walsh |
| 5,006,542 | A | 4/1991 | Hall et al. |
| 5,145,790 | A | 9/1992 | Mattingly et al. |
| 5,411,972 | A | 5/1995 | Komoto et al. |
| 5,413,891 | A | 5/1995 | Matsuura et al. |
| 5,532,371 | A | 7/1996 | Komoto et al. |
| 5,703,099 | A | 12/1997 | Hamanaka et al. |
| 6,057,408 | A | 5/2000 | Winter et al. |
| 6,150,413 | A | 11/2000 | Bernardon et al. |
| 6,376,546 | B1 | 4/2002 | Shoda et al. |
| 6,417,212 | B1 | 7/2002 | Brooks et al. |
| 7,056,942 | B2 | 6/2006 | Hildesheim et al. |
| 7,067,507 | B2 | 6/2006 | Pullet et al. |
| 7,737,135 | B2 | 6/2010 | Luker et al. |
| 8,003,703 | B2 | 8/2011 | Bonnert et al. |
| 8,008,350 | B2 | 8/2011 | Luker et al. |
| 8,022,248 | B2 | 9/2011 | Bonnert et al. |
| 2003/0050320 | A1 | 3/2003 | Hashimoto et al. |
| 2004/0029933 | A1 | 2/2004 | Zhao et al. |
| 2004/0097555 | A1 | 5/2004 | Ohkawa et al. |
| 2004/0220237 | A1 | 11/2004 | Fu et al. |
| 2005/0239881 | A1 | 10/2005 | Dunn et al. |
| 2006/0211765 | A1 | 9/2006 | Pairaudeau et al. |
| 2006/0264435 | A1 | 11/2006 | Bonnert et al. |
| 2006/0293352 | A1 | 12/2006 | Bonnert et al. |
| 2007/0249686 | A1 | 10/2007 | Bonnert et al. |
| 2008/0114002 | A1 | 5/2008 | Bonnert et al. |
| 2008/0132480 | A1 | 6/2008 | Luker et al. |
| 2008/0255150 | A1 | 10/2008 | Luker |
| 2008/0293775 | A1 | 11/2008 | Bonnert et al. |
| 2009/0012151 | A1 | 1/2009 | Bonnert et al. |
| 2009/0036535 | A1 | 2/2009 | Luker et al. |
| 2009/0149448 | A1 | 6/2009 | Alcaraz et al. |
| 2009/0192163 | A1 | 7/2009 | Luker et al. |
| 2010/0160285 | A1 | 6/2010 | Luker et al. |
| 2011/0152374 | A1 | 6/2011 | Luker et al. |

FOREIGN PATENT DOCUMENTS

| | | |
|---|---|---|
| CH | 432119 | 9/1967 |
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |

(Continued)

OTHER PUBLICATIONS

Vippagunta, et al. Advanced Drug Delivery Reviews 48 (2001) 3-26.*
Amin et al., "The Fries Reaction: Part VI - the rearrangement of aryl p-toluene-sulphonates & a convenient method for synthesis of hydroxyl-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.
AstraZeneca AB. WO03066046 & WO03066047, "The use of indole-3-acetic acids as CRTH2 receptor antagonists". *Expert Opin Ther. Patents* 14(1):125-128 (2004).
Baliah et al., "Fries rearrangement of the benzenesulphonates of xylenols", *Recueil des Travaux Chimiques des Pays-Bas*, vol. 80, 1961, pp. 139-148.

(Continued)

*Primary Examiner* — Shawquia Young
(74) *Attorney, Agent, or Firm* — Fish & Richardson P.C.

(57) ABSTRACT

The invention relates to substituted phenoxyacetic acids as useful pharmaceutical compounds for treating respiratory disorders, pharmaceutical compositions containing them, and processes for their preparation.

6 Claims, No Drawings